United States Patent
Hong et al.

(10) Patent No.: US 11,055,304 B2
(45) Date of Patent: Jul. 6, 2021

(54) SYSTEM AND METHOD FOR DIFFERENTIAL ANALYSIS

(71) Applicant: BRANDEIS UNIVERSITY, Waltham, MA (US)

(72) Inventors: Pengyu Hong, Waltham, MA (US); Yuanzhe Bei, Waltham, MA (US)

(73) Assignee: BRANDEIS UNIVERSITY, Waltham, MA (US)

( * ) Notice: Subject to any disclaimer, the term of this patent is extended or adjusted under 35 U.S.C. 154(b) by 191 days.

(21) Appl. No.: 15/518,403

(22) PCT Filed: Oct. 16, 2015

(86) PCT No.: PCT/US2015/055959
§ 371 (c)(1),
(2) Date: Apr. 11, 2017

(87) PCT Pub. No.: WO2016/061466
PCT Pub. Date: Apr. 21, 2016

(65) Prior Publication Data
US 2017/0308594 A1     Oct. 26, 2017

Related U.S. Application Data

(60) Provisional application No. 62/065,415, filed on Oct. 17, 2014.

(51) Int. Cl.
*G06F 16/25* (2019.01)
*G16B 40/00* (2019.01)
*G06F 17/18* (2006.01)

(52) U.S. Cl.
CPC .............. *G06F 16/25* (2019.01); *G06F 17/18* (2013.01); *G16B 40/00* (2019.02)

(58) Field of Classification Search
None
See application file for complete search history.

(56) References Cited

U.S. PATENT DOCUMENTS

2002/0169562 A1     11/2002  Stephanopoulos et al.
2006/0141489 A1 *    6/2006  Allison .................... G06F 19/20
                                                                435/6.16

(Continued)

OTHER PUBLICATIONS

The International Search Report and Written Opinion dated Jan. 12, 2016 for International Application No. PCT/US2015/055959.

(Continued)

*Primary Examiner* — Thu N Nguyen
(74) *Attorney, Agent, or Firm* — Quarles & Brady LLP

(57) ABSTRACT

The present disclosure includes systems and methods for performing a plurality of base statistical analysis on a dataset to yield multiple, different base statistics with respect to a first predetermined number of features. The dataset and the base statistics can be used to find a transformation that determines significant features while controlling a false discovery rate (FDR) to be below a target FDR threshold ($\Psi$), wherein a second predetermined number of features are assumed to be independent from each other. Using the transformation, a composite index can be generated that represents a synthesis of the base statistics and a report can be generated that indicates at least the relative presence of the significant features in the dataset using the composite index.

24 Claims, 9 Drawing Sheets

(56) References Cited

U.S. PATENT DOCUMENTS

2009/0106172 A1* 4/2009 Heckerman ............ G06N 7/005
                                                706/12
2012/0134966 A1   5/2012 Blelloch et al.
2017/0218454 A1*  8/2017 Plaisier ................ C12Q 1/6886

OTHER PUBLICATIONS

Storey, "The Positive False Discovery Rate: A Bayesian Interpretation and the q-Value" In: The Annals of Statistics, 2003, vol. 31, No. 6, [online][retreived on Dec. 7, 2015 (Dec. 7, 2015)] Retrieved from the Internet <URL: https://projecteuclid.org/euclid.aos/1074290335>, entire document, especially Abstract; p. 2015, 2017, 2032, 2033.

* cited by examiner

SYSTEM AND METHOD FOR DIFFERENTIAL ANALYSIS

CROSS-REFERENCE TO RELATED APPLICATIONS

This is application represents the U.S. National Stage of International Application No. PCT/US2015/055959, filed Oct. 16, 2015 which is based on, claims priority to and incorporates herein by reference in its entirety U.S. Provisional Application Ser. No. 62/065,415 filed Oct. 17, 2014 and entitled "System and Method for Controlling False Discovery Rates."

BACKGROUND

The present disclosure relates to systems and methods for differential analysis, i.e., detecting DEFs (features that are differentially regulated or behave differentially between conditions), which plague the processing of high-dimensional datasets, such as genome-wide datasets. More particularly, the present disclosure relates to systems and methods for integrating multiple attributes about being differentially regulated, each of which can be calculated by some statistical hypothesis test, to robustly detect DEFs under a user-defined false discovery rate (FDR) constraint as an optimization problem.

Systematic observation, experimentation, measurement, and data collection is fundamental to traditional process of scientific discovery. As science and industry builds and utilizes greater tools of observation, experimentation, and measurement, data collection and management have become paramount. For example, instruments, such as telescopes, high-energy particle accelerators, gene sequencing machines, and the like can generate massive datasets from observation of complex physical systems. When managing and/or processing very-large datasets, the amount of errors, such as false positives or false negatives, can greatly diminish the effectiveness of any system or method for analyzing such data. It is hence essential to control FDR.

FDR control has become a key component of systems and methods for identifying DEFs in analyzing large datasets, such as genome-wide datasets. FDR was first introduced by Benjamini and Hochberg to correct for multiple comparisons and control the expected portion of false positives called "significant" among the tests. It is now been widely practiced in analyzing genome-wide datasets generated by high-throughput technologies, such as DNA microarray data, RNA-seq, and the like. The Benjamini-Hochberg (BH) procedure (Benjamini, Y. and Y. Hochberg, Controlling the False Discovery Rate: A Practical and Powerful Approach to Multiple Testing. Journal of the Royal Statistical Society. Series B (Methodological), 1995. 57(1): p. 289-300) and the Storey procedure (Storey, J. D., A direct approach to false discovery rates. Journal of the Royal Statistical Society Series B, 2002. 64(3): p. 479-498 and Storey, J. D. and R. Tibshirani, Statistical significance for genomewide studies. Proc Natl Acad Sci USA, 2003. 100(16): p. 9440-5) are two of the most well-known FDR controlling procedures.

The existing DEF detection approaches rely on a selected statistical hypothesis test in each analysis run. Each statistical hypothesis test generates a single type of statistic, which will be referred to herein as a "base statistic" or attributes, to statistically assess whether a feature is differentially regulated between two conditions. For example, the t-test (Student, The Probable Error of a Mean. Biometrika, 1908. 6(1): p. 1-25) and the Wilcoxon ranksum test (Wilcoxon, F., Individual Comparisons by Ranking Methods. Biometrics Bulletin, 1945. 1(6): p. 80-83) (also known as the Mann-Whitney U test, referred as the ranksum test in the rest of this disclosure for conciseness) are two of the most well-known tests for assessing if a feature is DEFs and have motivated the development of several variants. For example, Significance Analysis of Microarrays (SAM) (Tusher, V. G., R. Tibshirani, and G. Chu, Significance analysis of microarrays applied to the ionizing radiation response. Proc Natl Acad Sci USA, 2001. 98(9): p. 5116-21 and U.S. Pat. No. 7,363,165) developed the corrected t-statistic and the corrected ranksum-statistic.

SAM implemented the Storey approach and has become a widely-practiced DEF detection technique for differential analysis using genome-wide datasets. SAM derives a delta ($\Delta$) index from the corrected t-statistic/ranksum-statistic for selecting significant features. Unfortunately, recent research (Bei, Y. and P. Hong. Significance Analysis by Minimizing False Discovery Rate. in IEEE International Conference on Bioinformatics and Biomedicine 2012. 2012. Philadelphia and Bei, Y. and P. Hong, A Novel Approach to Minimize False Discovery Rate in Genome-Wide Data Analysis. BMC Systems Biology, 2013. 7(S4).) has demonstrated problems with the use of the delta index. As an alternative, a method referred to as the "miFDR" was proposed to overcome the problems of the delta index. However, like other existing approaches, miFDR uses one selected base statistic in each analysis run and, thus, can be hampered by datasets with substantial variability that cannot be handled with the use of a single base statistic.

Each of those base statistics has its own advantages and disadvantages in assessing DEFs. For example, the t-test examines the difference in mean values between two groups under the normal distribution assumption. The ranksum test considers the ranks of the sample values, but does not take full advantage of their values. When normality holds, the t-test usually performs very well. However, if outliers exist, the ranksum test will less likely to be affected as it compares ranks rather than values. Either the t-test or the ranksum test has its own advantages over the other. In real-life applications, different features in the same dataset can be governed by many different types of distributions. The distributions of some features can be more complex than simple distributions (e.g., Gaussian, Poisson, negative binomial, etc.) that are assumed in many statistical tests. Thus these tests can have substantial shortcomings in real-world situations.

It would therefore be desirable to provide a system and method for detecting DEFs under a user-defined FDR threshold, which is less prone to the shortcomings of a given statistical test and, thereby, more robust.

SUMMARY

The present disclosure overcomes the aforementioned drawbacks by providing a system and method that integrates multiple base statistics into a Composite-Index, and use the Composite-Index to select significant features, for example, to improve DEF detection constrained by a user-defined FDR cutoff in large dataset analysis, such as genomic datasets. To integrate the multiple base statistics appropriately in the context of differential analysis, the integration may be formulated as an optimization problem. An algorithm is provided, referred to herein as Composite-Cut, to detect DEFs and control FDR using a manifest of Composite-Index. Experimental results show that Composite-Cut is consistently and significantly more robust than traditional methods. The implementation may assume features are independent from each other and use multiple base statistics for each feature to increase the chance of detecting features that behave differentially between conditions while controlling the FDR under a user-defined threshold. Without loss of generality, Composite-Cut assumes that K basic statistics can be calculated for each feature in a given dataset.

The approach presented herein can be geometrically interpreted as treating each feature as a point in the multi-dimensional space of those K basic statistics, and learning a discriminant function f( ), which takes multiple base statistics as the input and outputs a single value, from a given dataset to specify a decision boundary between DEFs and non-DEFs in that space. In other words, each basic statistic provides a certain point-of-view about differential expression, which is then integrated by f( ) to produce a more comprehensive view. Therefore an alternative name for Composite-Index can be Discriminant-Index, and another appropriate name for the Composite-Cut algorithm can be Discriminant-Cut.

In accordance with one aspect of the disclosure, a computer system for analyzing datasets is disclosed that includes a non-transitory, computer-readable, storage medium having stored thereon a dataset having data that corresponds to a number of features and having stored thereon a plurality of base statistical analysis on the dataset to yield multiple, different base statistics with respect to a first predetermined number of features. The system also includes a processor having access to the non-transitory computer-readable storage medium to access the dataset and the base statistics and having access to instructions that, when executed by the processor, cause the processor to use the dataset and the base statistics to find a transformation that determines significant features while controlling a false discovery rate (FDR) to be below a target FDR threshold ($\Psi$), wherein a second predetermined number of features are assumed to be independent from each other. The processor is also caused to generate, using the transformation, a composite index that represents a synthesis of the base statistics. The processor is further caused to generate a report indicating at least the relative presence of the significant features in the dataset using the composite index.

In accordance with another aspect of the disclosure, a microarray analysis system is disclosed that includes a microarray configured to hold a biological material to assay the biological material and generate a dataset about the biological material based thereon. The system also includes a processor configured to perform a plurality of base statistical analysis on the dataset to yield multiple, different base statistics with respect to a first predetermined number of features and use the dataset and the base statistics to find a transformation that determines significant features while controlling a false discovery rate (FDR) to be below a target FDR threshold ($\Psi$), wherein a second predetermined number of features are assumed to be independent from each other. The processor is further configured to generate, using the transformation, a composite index that represents a synthesis of the base statistics and generate a report indicating at least the relative presence of the significant features in the dataset using the composite index.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

As will be described, the present disclosure provides systems and methods for differential analysis that utilizes a Composite-Index, which integrates multiple base statistics, to select significant features from a dataset. To integrate multiple statistics appropriately in the context of DEF detection while controlling FDR, the systems and methods of the present disclosure may treat the integration as an optimization problem. For example, an algorithm, referred to here as the Composite-Cut algorithm or technique, is provided to detect DEFs under a FDR constraint using a special manifest of Composite-Index.

Again, the approach presented herein can be geometrically interpreted as treating each feature as a point in the multi-dimensional space of those K basic statistics, and learning a discriminant function f( ) from a given dataset to specify a decision boundary between differentially expressed features (DEFs) and non-DEFs in that space. In other words, each basic statistic provides a certain point-of-view about differential expression, which is then integrated by f( ) to produce a more comprehensive view. Therefore an alternative name for Composite-Index can be Discriminant-Index. The Composite-Cut algorithm chooses the discriminant function f( ) from the linear function family. Another appropriate name for the Composite-Cut algorithm can be Discriminant-Cut.

Figure 1:
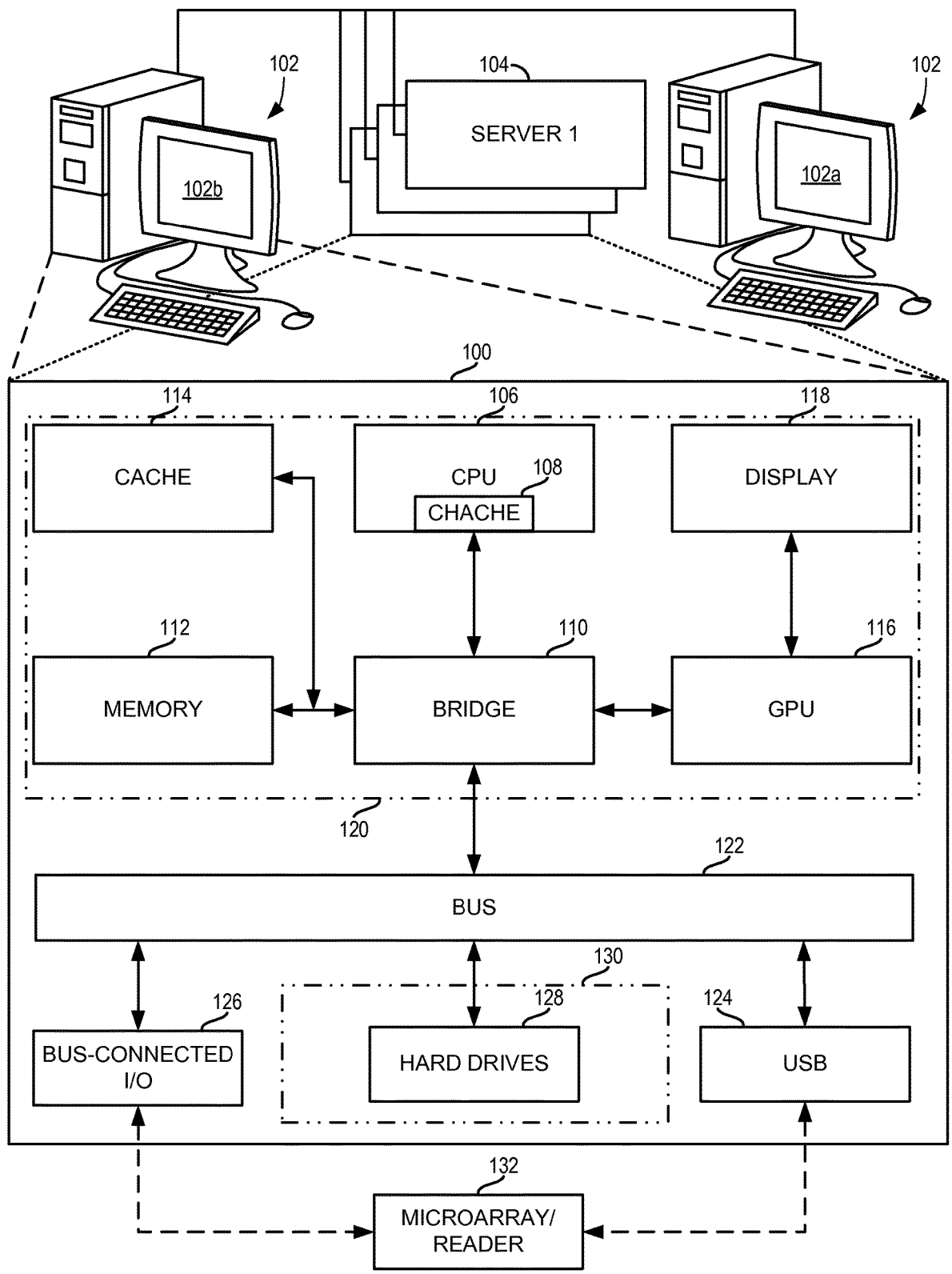
FIG. 1 is a schematic illustration of a system that may be configured for use in accordance with the present disclosure.

The systems and methods of the present disclosure can be implemented using a computer hardware architecture 100, such as illustrated in FIG. 1. Specifically, referring to FIG. 1, a general hardware architecture 100 is illustrated that is representative of the hardware architecture employed in both workstations 102 and servers 104. The hardware architecture 100 includes one or more CPUs 106. Trends in CPU designs have evolved over the years and have included increasing clock speeds, increasing density per chip, increasing chips per die, and increasing processors that together form the CPU 108. While each advancement has improved performance, computer hardware architecture since the earliest designs generally include a CPU 106 and one or more associated caches 18.

The CPU 106 is generally connected through a bridge 110 to memory 112 and, in some cases, an additional non-local cache 114. While memory and cache design evolutions have been great over the years, they generally adhere to the concept of placing one or more levels of comparatively fast random access memory in close proximity (access proximity) to the CPU 106. In more recent times, dedicated graphics processing units (GPUs) 116 have been adapted from processors utilized to simply drive a display 118 to a secondary, specialized processor that the CPU 106 can utilize to offload tasks fitting the specialized capabilities of the CPU 106, such as transcoding operations and many others. In any case, the general computer architecture 100, regardless of whether the system is a workstation 102 or server 104, regardless of whether the computer architecture is from the 1990s or more recent times, provides a CPU 106 and memory 112 and may be supplemented by secondary processing and memory components, such as a GPU 116 and various caches 108, 114 dedicated to particular situations. In this regard, the above-described components may be conceptualized as a CPU/memory sub-system 120.

The computer architecture 100 also includes a bus or multiple buses 122 that connect the above-described CPU/memory sub-system 120 to other, slower components of the computer architecture 100. For example, the buses 122 may provide connections to a universal serial bus (USB) hub or controller 124 and/or dedicated, bus-connected I/O devices 126. Of course, I/O connections may vary substantially; however, in most cases, the bus 122 provides connections to one or more hard drives 128. These hard drives 128 may take many forms and, more recently, include hardware advances such as solid-state drives, but are uniformly present in workstations or personal computers 102 and servers 104. This is because all traditional notions of computer architecture can be conceptualized as, at a minimum, including a CPU/memory sub-system 120 and a mass-storage sub-system 130.

The above-described computer architecture 100 may be specifically adapted for various applications. For example, the above-described computer architecture 100 of the workstation 102 or server 104 may be adapted with specialized hardware or software for applications, such as genome datasets. For example, the bus-connected I/O 126 or USB controller/connections 124 may be coupled to a reader for analyzing microarrays 132 and the like. That is, the above-described system may be specifically adapted for use with microarrays 132 that are formed as grid of DNA segments configured to test and map DNA fragments, antibodies, or proteins. The microarray(s) 132 may be formed as a multiplex lab-on-a-chip including an array formed on a solid substrate to assays large amounts of biological material using high-throughput screening miniaturized, multiplexed, and parallel processing and detection methods.

Regardless of the particular architecture 100 or application, the present disclosure provides methods, algorithms, and processing techniques that may be embodied as computer-readable programs that can be stored in memory, such as the above-described memory 112 or hard drive 128, be accessible by a processor or controller, such as the above-described CPU 106 or GPU 116, and be executed by the processor or controller to yield improved control of DEF detection and, thereby, improved results when processing and analyzing datasets.

Composite-Index and Power Maximization Constrained by FDR

Assuming that K different base statistics $\vec{d}_i = [d_i^1, d_i^2, \ldots, d_i^K]$ are obtained for each of the total M features in a dataset, we apply a transformation $f(\bullet)$, which will be determined in implementation, to obtain the Composite-Index as $\mathbb{C} = \{c_i = f(\vec{d}_i)\}_{i=1 \ldots M}$. Without losing generality, we request that the one-side significance of the Composite-Index increases monotonically with respect to its absolute value. The correlations between base statistics can be complex, which will result in a complex Composite-Index distribution. Hence, it may not be productive to determine the p-value of a particular Composite-Index value in an analytical way. Hence, we use the Composite-Index cut-off $\tau$ to define the reject regions as $\Gamma = (\tau, \infty)$, for identifying significantly up-regulated DEFs as:

$$D(\Gamma, f(\bullet)) = \{i | c_i \in \Gamma, c_i \in \mathbb{C}\} \qquad \text{Eqn. (1)}$$

Let $FDR(\Gamma, f(\bullet))$ denote the corresponding FDR of $D(\Gamma, f(\bullet))$. Our goal is to find $f(\bullet)$ and $\Gamma$ so that the number of the identified DEFs is maximized while $FDR(\Gamma, f(\bullet))$ is under controlled by a user-defined threshold $\Psi$. It should be noted that F can be absorbed into $f(\bullet)$. This problem can be mathematically represented as:

$$\max_{\Gamma, f(\bullet)} |D(\Gamma, f(\bullet))| \text{ Satisfy } FDR(\Gamma, f(\bullet)) < \Psi \qquad \text{Eqn. (2)}$$

Composite-Cut Algorithm

As an initial point of consideration, the Composite-Index can be conceptualized as a linear combination of two base statistics. For example, the corrected t-test statistic and the corrected ranksum-test statistic can be used. Specifically, without losing generality, we assume that the samples are divided into two groups, X and Y with $N_X$ and $N_Y$ samples, respectively. Let $\overline{X}_i$ and $\overline{Y}_i$ denote the average values of the i-th feature in X and Y, respectively. Both the traditional t-statistic and ranksum-statistic can be written in the form of $g_i = v_i/s_i$, where:

In traditional t-statistic: $v_i = \overline{X}_i - \overline{Y}_i$ and $s_i = \{[\sum_{x_{im} \in X}(x_{im} - \overline{X}_i)^2 + \sum_{y_{in} \in Y}(y_{in} - \overline{Y}_i)^2](1/N_X + 1/N_Y)/(N_X + N_Y - 2)\}^{1/2}$;

In traditional ranksum-statistic: $v_i = \overline{R}_i^X - N_X(N_X + N_Y + 1)/2$ and $s_i = N_X N_Y(N_X + N_Y + 1)/12$; where $\overline{R}_i^X$ is the sum of the ranks of the i-th feature from X (the measurements from X and Y are merged and then ranked from lowest to highest).

One major disadvantage of these traditional statistics is that the estimation of $s_i$ is very unstable when the sample size is relatively small, which is quite common in gene expression analysis. To solve this problem, SAM introduced a fudge factor $s_0$ to the denominator. Therefore, a corrected statistic can be represented as $d_i = v_i/(s_i + s_0)$. The factor $s_0$ is chosen using $\{s_i\}$ to minimize the coefficient of variation of $d_i$. As a result, the variance of $d_i$ will be independent to the expression level. Further reference to Chu, G., et al., Significance Analysis of Microarrays—Users guide and technical document ver 4.0 2011, which is incorporated by reference herein in its entirety, may be made for additional information about calculating $s_0$. As used herein, $d_i^T$ and $d_i^R$ indicate the corrected t-statistic and the corrected ranksum-statistic of the i-th feature, respectively.

Let the NULL hypothesis of a genomic feature be that it is not a DEF. Assume features are independent, and we are testing M identical independent hypotheses (one for each feature) with M independent Composite-Indexes. Here $R = R(\Gamma)$ is an observable variable indicating the number of hypotheses rejected by $\Gamma$ (i.e., DEFs) and $V = V(\Gamma)$ is a hidden variable indicating the number of true NULL hypotheses rejected by $\Gamma$ (i.e., falsely identified DEFs). We can write down the FDR according to (Storey 2002) as a function of $\Gamma$:

$$FDR(\Gamma) = E\left[\frac{V(\Gamma)}{R(\Gamma)} \mid R(\Gamma) > 0\right] P(R(\Gamma) > 0) = \quad \text{Eqn. (3)}$$

$$P(NULL \mid C \in \Gamma, R(\Gamma) > 0) \cdot P(R(\Gamma) > 0)$$

where C is a variable of Composite-Index. It can be rewritten as the following via the Bayes rule:

$$FDR(\Gamma) = \quad \text{Eqn. (4)}$$

$$P(NULL) \cdot P(C \in \Gamma \mid NULL, R(\Gamma) > 0) / P(C \in \Gamma \mid R(\Gamma) > 0) \cdot$$

$$P(R(\Gamma) > 0) + \frac{P(NULL) \cdot P(C \in \Gamma \mid NULL, R(\Gamma) = 0)}{P(C \in \Gamma \mid R(\Gamma) > 0)}.$$

$$P(R(\Gamma) = 0) = \frac{P(NULL) \cdot P(C \in \Gamma \mid NULL)}{P(C \in \Gamma \mid R(\Gamma) > 0)}$$

Eqn. (4) utilizes the fact that $P(C \in \Gamma | NULL, R(\Gamma)=0)=0$ because no hypothesis is rejected when $R(\Gamma)=0$. Below we explain non-parametric methods for estimating $P(C \in \Gamma | NULL)$, $P(NULL)$, and $P(C \in \Gamma | R(\Gamma) > 0)$, which are needed for estimating $FDR(\Gamma)$ given a Composite-Index set $\mathbb{C}$ derived from a given dataset using a fixed $f(\bullet)$.

The term $P(C \in \Gamma | NULL)$ is the probability of $C > \tau$ when NULL is true. It is equivalent to the p-value of $\tau$, which we indicate as $p_\tau$. The distribution of Composite-Index, depending on both the distributions of basic attributes and the function $f(\bullet)$ can be extremely complex. Hence it may not feasible to determine the p-value of a particular Composite-Index value in an analytical form. We therefore estimate $P(C \in \Gamma | NULL)$ by adopting the non-parametric method proposed in (see Tusher, V. G., R. Tibshirani, and G. Chu, Significance analysis of microarrays applied to the ionizing radiation response. Proc Natl Acad Sci USA, 2001. 98(9): p. 5116-21, which is incorporated herein by reference in its entirety), which allows us to better explore distributional structure in a data-dependent manner. This method randomly permutes the original dataset B times to generate the null control, and estimates $P(C \in \Gamma | NULL)$ as:

$$\hat{P}(C \in \Gamma \mid NULL) = \hat{p}_\tau = \frac{\hat{\mathbb{E}}_b(|\{c_{i,b}^* \mid c_{i,b}^* \in \Gamma \cap \mathbb{C}_b^*\}|)}{M} \quad \text{Eqn. (5)}$$

where $c_{i,b}^*$ is the Composite-Index of the i-th feature in the b-th ($1 \leq b \leq B$) permutation and $\mathbb{C}_b^* = \{c_{i,b}^*\}_{i=1 \ldots M}$. The function $\hat{\mathbb{E}}_b(\bullet)$ uses all B permutated datasets to estimate the expected number of non-DEFs that are incorrectly identified as DEFs. A reasonable choice of $\hat{\mathbb{E}}_b(\bullet)$ is the median function. When the number of samples is large enough, the permutated data forms a good approximation to the NULL distribution as $B \to \infty$, and hence we have $\lim_{B \to \infty} \hat{p}_\tau \to p_\tau$.

It is expected that $P(NULL) \cdot M$ features are non-DEFs (i.e., true NULL hypotheses). Assuming that all features are independent, the p-values of these $P(NULL) \cdot M$ features should be uniformly distributed between 0 and 1. Therefore, for a p-value cutoff $\lambda \in (0,1)$, we should expect that there are $(1-\lambda) \cdot P(NULL) \cdot M$ non-DEFs whose p-values are greater than $\lambda$. Since it is possible for some true DEFs to have p-values greater than $\lambda$, it is expected that $(1-\lambda) \cdot P(NULL) \cdot M \leq |\{c_i | p(c_i) \geq \lambda, c_i \in \mathbb{C}\}|$ when M is large enough and $\lambda$ is well-chosen, where $p(c_i)$ is the p-value of a Complex-Index $c_i$ in the Composite-Index set $\mathbb{C}$ of the given dataset. Let $\Gamma_\lambda$ be the rejection region that rejects Composite-Indexes whose p-values are smaller than $\lambda$. In practice, $\Gamma_\lambda$ can be estimated as the region that rejects percentile of elements in the permutation set $\{\mathbb{C}_b^*\}_{b=1 \ldots B}$. We have a conservative estimation of $P(NULL)$ which is:

$$\hat{P}(NULL) = \quad \text{Eqn. (6)}$$

$$\frac{|\{c_i \mid p(c_i) \geq \lambda, c_i \in \mathbb{C}\}|}{(1-\lambda) \cdot M} = \frac{|\{c_i \mid c_i \notin \Gamma_\lambda, c_i \in \mathbb{C}\}|}{(1-\lambda) \cdot M} = \frac{w_{\mathbb{C}}(\Gamma_\lambda)}{(1-\lambda) \cdot M}$$

where $w_{\mathbb{C}}(\Gamma) = |\{c_i | c_i \notin \Gamma, c_i \in \mathbb{C}\}|$ is an observed value of the variable $W(\Gamma)$ on a fixed $\mathbb{C}$. We conservatively set $\lambda=50\%$ and truncate $\hat{P}(NULL)$ at 1 because a probability should never exceed 1.

Estimate $P(C \in \Gamma | R(\Gamma) > 0)$

The probability $P(C \in \Gamma | R(\Gamma) > 0)$ can be naturally estimated as:

$$\hat{P}(C \in \Gamma \mid R(\Gamma) > 0) = \frac{|\{c_i \mid c_i \in \Gamma, c_i \in \mathbb{C}\}| \vee 1}{M} = \frac{r_{\mathbb{C}}(\Gamma_\lambda) \vee 1}{M} \quad \text{Eqn. (7)}$$

where $r_{\mathbb{C}}(\Gamma) = M - w_{\mathbb{C}}(\Gamma)$ is an observed value of the variable $R(\Gamma)$ on a fixed $\mathbb{C}$, and $r_{\mathbb{C}}(\Gamma) \vee 1 = r_{\mathbb{C}}(\Gamma)$ if $r_{\mathbb{C}}(\Gamma) > 0$, otherwise 1. The term $r_{\mathbb{C}}(\Gamma) \vee 1$ prevents the estimated FDR from being undefined due to having 0 as the denominator. Plugging Eqn. (5-7) into Eqn. (4), we have the estimated FDR as:

$$\widehat{FDR}_{\lambda,\mathbb{C}}(\Gamma) = \frac{\frac{w_{\mathbb{C}}(\Gamma_\lambda)}{(1-\lambda) \cdot M} \cdot \hat{p}_\tau}{\frac{r_{\mathbb{C}}(\Gamma) \vee 1}{M}} = \frac{w_{\mathbb{C}}(\Gamma_\lambda) \cdot \hat{p}_\tau}{(1-\lambda)\{r_{\mathbb{C}}(\Gamma) \vee 1\}} \quad \text{Eqn. (8)}$$

If the number of permutation is large enough, $r_{\mathbb{C}}(\Gamma) \vee 1$ will effectively set the estimated FDR as 0 when $r_{\mathbb{C}}(\Gamma)=0$ because, on expectation, the Composite-Indexes of the permuted data should not be more likely to be rejected by $\Gamma$ than those of the original data. Thus we have $\hat{p}_\tau = \hat{\mathbb{E}}_b(|\{c_{i,b}^* \in \Gamma, c_{i,b}^* \in \mathbb{C}_b^*\}|)/M \leq |\{c_i | c_i \in \Gamma, c_i \in \mathbb{C}\}|/M = r_{\mathbb{C}}(\Gamma)/M = 0$, which effectively sets $\widehat{FDR}_{\lambda,\mathbb{C}}(\Gamma) = 0$.

Theorems 1 and 2 below justify that Eqn. (8) is a sound approximation to the real FDR for the large feature and finite feature scenarios. In Theorem 1, we take the expectation of the estimated FDR w.r.t. the datasets sampled from the population of interest, and, with a little bit abuse of notation, let $\mathbb{C}$ be a random variable representing the Composite-Index set of a randomly sampled dataset.

Theorem 1.

Given a fixed attribute integration function $f(\bullet)$, a well-chosen $\lambda$ and a rejection region $\Gamma \subset \Gamma_\lambda$, it holds that $\lim_{B \to \infty} E_{\mathbb{C}}[\widehat{FDR}_{\lambda,\mathbb{C}}(\Gamma)] \geq FDR(\Gamma)$, where $E_{\mathbb{C}}$ is the expectation w.r.t. the random variable $\mathbb{C}$.

Proof: Recall Eqn. (3), the true FDR for a rejection region Γ can be written as:

$$FDR(\Gamma) = E\left[\frac{V(\Gamma)}{R(\Gamma) \vee 1}\right] \quad \text{Eqn. (S1)}$$

where V(Γ) and R(Γ) are the variables representing the number of false positives and the total rejections w.r.t. a fixed Γ. The expectation is taken w.r.t. the datasets sampled from the population of interest. With a slight modification, we let $\mathbb{C}$ be a random variable representing the Composite-Index set of a randomly sampled dataset. Given λ and Γ=(τ, +∞), we have:

$$E_{\mathbb{C}}[\widetilde{FDR}_{\lambda,\mathbb{C}}(\Gamma)] = E_{\mathbb{C}}\left[\frac{\frac{w_{\mathbb{C}}(\Gamma_\lambda)}{(1-\lambda)} \cdot \hat{p}_\tau}{r_{\mathbb{C}}(\Gamma) \vee 1}\right] = E\left[\frac{\frac{w(\Gamma_\lambda)}{(1-\lambda)} \cdot \hat{p}_\tau}{R(\Gamma) \vee 1}\right] \quad \text{Eqn. (S2)}$$

where $w_{\mathbb{C}}(\Gamma_\lambda)$ and $r_{\mathbb{C}}(\Gamma)$ are observed values of W(Γ$_\lambda$) and R(Γ) on a fixed $\mathbb{C}$, respectively. Considering the difference between Eqn. (S2) and Eqn. (S1), we have:

$$E_{\mathbb{C}}[\widetilde{FDR}_{\lambda,\mathbb{C}}(\Gamma)] - FDR(\Gamma) = E\left[\frac{\frac{w(\Gamma_\lambda)}{1-\lambda} \cdot \hat{p}_\tau - V(\Gamma)}{R(\Gamma) \vee 1}\right] = \quad \text{Eqn. (S3)}$$

$$E\left[\frac{\frac{w(\Gamma_\lambda)}{1-\lambda} \cdot \hat{p}_\tau - V(\Gamma)}{R(\Gamma) \vee 1} \,\middle|\, R(\Gamma) > 0\right] \cdot P(R(\Gamma) > 0) +$$

$$E\left[\frac{\frac{w(\Gamma_\lambda)}{1-\lambda} \cdot \hat{p}_\tau - V(\Gamma)}{R(\Gamma) \vee 1} \,\middle|\, R(\Gamma) = 0\right] \cdot P(R(\Gamma) = 0)$$

Conditioning on R(Γ), it follows that:

$$E\left[\frac{\frac{w(\Gamma_\lambda)}{1-\lambda} \cdot \hat{p}_\tau - V(\Gamma)}{R(\Gamma) \vee 1} \,\middle|\, R(\Gamma)\right] = \quad \text{Eqn. (S4)}$$

$$\frac{E\left[\frac{w(\Gamma_\lambda)}{1-\lambda} \cdot \hat{p}_\tau \,\middle|\, R(\Gamma)\right] - E[V(\Gamma) \mid R(\Gamma)]}{R(\Gamma) \vee 1}$$

By independence, since Γ⊂Γ$_\lambda$, we have R(Γ$_\lambda$)=R(Γ)+R(Γ$_\lambda$-Γ) where R(Γ$_\lambda$-λ)=|{C|C∈Γ$_\lambda$-Γ}|. Note that R(Γ$_\lambda$-Γ) is independent to R(Γ) because Γ∩(Γ$_\lambda$-Γ)=∅. Hence E[W(Γ$_\lambda$)|R(Γ)]=E[M−R(Γ)−R(Γ$_\lambda$-Γ)|R(Γ)]=M−E[R(Γ$_\lambda$-Γ)]−R(Γ) is a linear non-increasing function of R(Γ). On the other hand, given R(Γ)>0, we have $$E[V(\Gamma) \mid R(\Gamma)] =$$

$$E\left[R(\Gamma) \cdot \frac{V(\Gamma)}{R(\Gamma)} \,\middle|\, R(\Gamma)\right] = R(\Gamma) \cdot E\left[\frac{V(\Gamma)}{R(\Gamma)} \,\middle|\, R(\Gamma)\right] = R(\Gamma) \cdot FDR(\Gamma)$$

is linear non-decreasing function of R(Γ) because FDR(Γ) is a constant value when Γ is fixed. Thus, we can define an convex function $$\varphi(x) = \left[\frac{M - x - E[R(\Gamma_\lambda - \Gamma)]}{1 - \lambda} \cdot \hat{p}_\tau - FDR(\Gamma) \cdot x\right] / x$$

and by Jensen's inequality on φ(R(Γ)) it follows that:

$$E\left[\frac{\frac{w(\Gamma_\lambda)}{1-\lambda} \cdot \hat{p}_\tau - V(\Gamma)}{R(\Gamma) \vee 1} \,\middle|\, R(\Gamma) > 0\right] = \quad \text{Eqn. (S5)}$$

$$E\left[\frac{\frac{w(\Gamma_\lambda)}{1-\lambda} \cdot \hat{p}_\tau - V(\Gamma)}{R(\Gamma)} \,\middle|\, R(\Gamma) > 0\right] =$$

$$E[\varphi(R(\Gamma)) \mid R(\Gamma) > 0] \geq \varphi(E[R(\Gamma) \mid R(\Gamma) > 0]) =$$

$$\frac{E\left[\frac{w(\Gamma_\lambda)}{1-\lambda} \cdot \hat{p}_\tau - V(\Gamma) \,\middle|\, R(\Gamma) > 0\right]}{E[R(\Gamma) \mid R(\Gamma) > 0]}$$

Since E[R(Γ)|R(Γ)=0]P(R(Γ)=0)=0 and thus E[R(Γ)]= E[R(Γ)|R(Γ)>0]P(R(Γ)>0), we have:

$$E\left[\frac{\frac{w(\Gamma_\lambda)}{1-\lambda} \cdot \hat{p}_\tau - V(\Gamma)}{R(\Gamma) \vee 1} \,\middle|\, R(\Gamma) > 0\right] \geq \quad \text{Eqn. (S6)}$$

$$\frac{E\left[\frac{w(\Gamma_\lambda)}{1-\lambda} \cdot \hat{p}_\tau - V(\Gamma) \,\middle|\, R(\Gamma) > 0\right]}{E[R(\Gamma)] / P(R(\Gamma) > 0)}$$

Let's turn to:

$$E\left[\frac{\frac{w(\Gamma_\lambda)}{1-\lambda} \cdot \hat{p}_\tau - V(\Gamma)}{R(\Gamma) \vee 1} \,\middle|\, R(\Gamma) = 0\right] = \quad \text{Eqn. (S7)}$$

$$E\left[\frac{\frac{w(\Gamma_\lambda)}{1-\lambda} \cdot \hat{p}_\tau - V(\Gamma)}{1} \,\middle|\, R(\Gamma) = 0\right]$$

Since E[R(Γ)|R(Γ)>0]≥1 and thus E[R(Γ)]=E[R(Γ)|R(Γ)>0]P(R(Γ)>0)≥P(R(Γ)>0), we can obtain:

$$E\left[\frac{\frac{w(\Gamma_\lambda)}{1-\lambda} \cdot \hat{p}_\tau - V(\Gamma)}{R(\Gamma) \vee 1} \,\middle|\, R(\Gamma) = 0\right] \geq \quad \text{Eqn. (S8)}$$

$$\frac{E\left[\frac{w(\Gamma_\lambda)}{1-\lambda} \cdot \hat{p}_\tau - V(\Gamma) \,\middle|\, R(\Gamma) = 0\right]}{E[R(\Gamma)] / P(R(\Gamma) > 0)}$$

Putting Eqn. (S7) and Eqn. (S8) into Eqn. (S3), we obtain:

$$E_{\mathbb{C}}[\widetilde{FDR}_{\lambda,\mathbb{C}}(\Gamma)] - FDR(\Gamma) \geq \quad \text{Eqn. (S9)}$$

$$\frac{E\left[\frac{w(\Gamma_\lambda)}{1-\lambda} \cdot \hat{p}_\tau - V(\Gamma) \,\middle|\, R(\Gamma) > 0\right] P(R(\Gamma) > 0) +}{E[R(\Gamma)] / P(R(\Gamma) > 0)} =$$

$$\frac{E\left[\frac{w(\Gamma_\lambda)}{1-\lambda} \cdot \hat{p}_\tau - V(\Gamma) \,\middle|\, R(\Gamma) = 0\right] P(R(\Gamma) = 0)}{E[R(\Gamma)] / P(R(\Gamma) > 0)} =$$

$$\frac{E\left[\frac{w(\Gamma_\lambda)}{1-\lambda} \cdot \hat{p}_\tau - V(\Gamma)\right]}{E[R(\Gamma)] / P(R(\Gamma) > 0)} = \frac{E\left[\frac{w(\Gamma_\lambda)}{1-\lambda} \cdot \hat{p}_\tau\right] - E[V(\Gamma)]}{E[R(\Gamma)] / P(R(\Gamma) > 0)}$$

Since $E[V(\Gamma)]=M\cdot P(C\in\Gamma\cap\text{NULL})=M\cdot P(\text{NULL})\cdot P(C\in\Gamma|\text{NULL})=M\cdot P(\text{NULL})\cdot p_\tau$ and $$\frac{w(\Gamma_\lambda)}{(1-\lambda)\cdot M} = \hat{P}_\lambda(\text{NULL}) \geq P(\text{NULL}) \Rightarrow W(\Gamma_\lambda) \geq (1-\lambda)\cdot M \cdot P(\text{NULL}),$$

we have:

$$E\left[\frac{w(\Gamma_\lambda)}{1-\lambda}\cdot \hat{p}_\tau - V(\Gamma)\right] \geq \qquad \text{Eqn. (S10)}$$

$$\frac{(1-\lambda)\cdot M\cdot P(\text{NULL})}{1-\lambda}\cdot \hat{p}_\tau - M\cdot P(\text{NULL})\cdot p_\tau =$$

$$M\cdot P(\text{NULL})\cdot(\hat{p}_\tau - p_\tau)$$

Plugging Eqn. (S10) into Eqn. (S9), and because $\lim_{B\to\infty}\hat{p}_\tau = p_\tau$, it holds that:

$$\lim_{B\to\infty} E_{\mathbb{C}}\left[\widehat{\text{FDR}}_{\lambda,\mathbb{C}}(\Gamma)\right] - FDR(\Gamma) = \qquad \text{Eqn. (S11)}$$

$$\lim_{B\to\infty}\left\{E_{\mathbb{C}}\left[\widehat{\text{FDR}}_{\lambda,\mathbb{C}}(\Gamma)\right] - FDR(\Gamma)\right\} \geq$$

$$\frac{M\cdot P(\text{NULL})}{E[R(\Gamma)]/P(R(\Gamma)>0)}\cdot (\lim_{B\to\infty}\hat{p}_\tau - p_\tau) = 0$$

Therefore the theorem holds ∎.

Theorem 2.

With probability 1, given a fixed attribute integration function $f(\bullet)$, a well-chosen $\lambda$ and a rejection region $\Gamma\subset\Gamma_\lambda$, it holds that $\lim_{M,B\to\infty}\{\widehat{\text{FDR}}_{\lambda,\mathbb{C}}(\Gamma)\}\geq FDR(\Gamma)$.

Proof: Recall Eqn. (4) that:

$$\widehat{\text{FDR}}_{\lambda,\mathbb{C}}(\Gamma) = \qquad \text{Eqn. (S12)}$$

$$\frac{\hat{P}(\text{NULL})\hat{P}(C\in\Gamma|\text{NULL})}{\hat{P}(C\in\Gamma|R(\Gamma)>0)} = \frac{w_{\mathbb{C}}(\Gamma_\lambda)\cdot \hat{p}_\tau}{(1-\lambda)\hat{P}(C\in\Gamma|R(\Gamma)>0)}$$

Let $g(\lambda)$ denote the power of rejection function on $[0,\lambda]$. Since $P(C\not\in\Gamma_\lambda|\text{NULL})=1-\lambda$ and $P(C\not\in\Gamma_\lambda|\overline{\text{NULL}})=1-g(\lambda)$, by the strong law of large numbers, we have $w_{\mathbb{C}}(\Gamma_\lambda)\to M\cdot\{P(\text{NULL})\cdot(1-\lambda)+[1-P(\text{NULL})]\cdot[1-g(\lambda)]\}$ almost surely. In addition, by the strong law of large numbers, we have $\hat{P}(C\in\Gamma|R(\Gamma)>0)\to P(C\in\Gamma|R(\Gamma)>0)$ almost surely. Thus, it holds that:

$$\lim_{M\to\infty}\{\widehat{\text{FDR}}_{\lambda,\mathbb{C}}(\Gamma)\} = \qquad \text{Eqn. (S13)}$$

$$\frac{\left[P(\text{NULL}) + [1-P(\text{NULL})]\cdot\frac{1-g(\lambda)}{1-\lambda}\right]\cdot \hat{p}_\tau}{P(C\in\Gamma|R(\Gamma)>0)} =$$

$$\frac{P(\text{NULL})\cdot\hat{p}_\tau}{P(C\in\Gamma|R(\Gamma)>0)} + \frac{[1-P(\text{NULL})]\cdot\frac{1-g(\lambda)}{1-\lambda}\cdot\hat{p}_\tau}{P(C\in\Gamma|R(\Gamma)>0)} \geq$$

$$\frac{P(\text{NULL})\cdot\hat{p}_\tau}{P(C\in\Gamma|R(\Gamma)>0)} \xrightarrow{B\to\infty}$$

$$\frac{P(\text{NULL})\cdot p_\tau}{P(C\in\Gamma|R(\Gamma)>0)} = FDR(\Gamma)$$

Therefore the theorem holds ∎.

Composite-Cut Algorithm Pseudo Code

As a simple start to implement Eqn. (2), we chose the attribute integration function $f(\bullet)$ from the linear function family: $f(s_1,\ldots,s_K)=\Sigma_{i=1}^{K}w_i s_i$, subject to $\Sigma_{i=1}^{K}w_i=1$ and $w_i\geq 0$. A simple algorithm, Composite-Cut (CC), was designed and implemented to search for the "ideal" $f(\bullet)$. CC performs an exhaustive search with an empirically decided resolution. The pseudo code is as the following:

$[f^+(\bullet),f^-(\bullet),\Gamma^+,\Gamma^-,\Delta^+,\Delta^-]=\text{Composite-Cut}(\mathbb{D},\Psi)$ Inputs:

$\mathbb{D}=\{d_i^{(k)}\}_{i=1\ldots M;k=1\ldots K}$ is the basic attribute set where i is the gene index and k is the basic attribute index.

$\Psi$ is the desired FDR (e.g., 0.05) chosen by the user.

Outputs:

$f^+(\bullet)$ and $f^-(\bullet)$ are the best feature integration functions for the up- and down-regulation, respectively.

$\Gamma^+$ and $\Gamma^-$ are the rejection regions of the up- and down-regulation, respectively.

$\Delta^+$ and $\Delta^-$ are significantly up- and down-DEFs, respectively.

Steps:

Initialize $\Delta^+\leftarrow\emptyset$, $\Delta^-\leftarrow\emptyset$.

Populate a candidate function set to cover the function space with an empirically decided resolution:

$\mathcal{F}_K=\{f(d_1,\ldots,d_K)=\Sigma_{i=1}^{K}w_i d_i|w_i\in\{0,0.1,\ldots,1\}, \Sigma_{i=1}^{K}w_i=1\}$ For each $f(\bullet)\in\mathcal{F}_K$:

Calculate Composite-Index set $\mathbb{C}\leftarrow\{c_i=f(d_i^{(1)},d_i^{(2)},\ldots,d_i^{(K)})\}$.

Use binary search to adjust $\Gamma=(\tau,+\infty)$ to maximize $D(\Gamma,f(\bullet))$ while making sure $\widehat{\text{FDR}}_{\lambda,\mathbb{C}}(\Gamma)<\Psi$. Eqn. (8) is used to estimate $\widehat{\text{FDR}}_{\lambda,\mathbb{C}}(\Gamma)$ and $\lambda$ is by default set to 0.5. If $\max_\Gamma D(\Gamma,f(\bullet))>|\Delta^+|$, let $\Gamma^+\leftarrow\text{argmax}_\Gamma D(\Gamma,f(\bullet))$, $f^+(\bullet)\leftarrow f(\bullet)$, and $\Delta^+\leftarrow\{i|c_i\in\Gamma^+, c_i\in\mathbb{C}\}$.

Use binary search to adjust $\Gamma=(-\infty,\tau)$ to maximize $D(\Gamma,f(\bullet))$ while making sure $\widehat{\text{FDR}}_{\lambda,\mathbb{C}}(\Gamma)<\Psi$. Eqn. (8) is used to estimate $\widehat{\text{FDR}}_{\lambda,\mathbb{C}}(\Gamma)$ and $\lambda$ is by default set to 0.5. If $\max_\Gamma D(\Gamma,f(\bullet))>|\Delta^-|$, let $\Gamma^-\leftarrow\text{argmax}_\Gamma D(\Gamma,f(\bullet))$, $f^-(\bullet)\leftarrow f(\bullet)$, and $\Delta^-\leftarrow\{i|c_i\in\Gamma^-, c_i\in\mathbb{C}\}$.

Return $f^+(\bullet),f^-(\bullet),\Gamma^+,\Gamma^-,\Delta^+,\Delta^-$.

For each candidate $f(\bullet)$, it calculates the corresponding Composite-Index set $\mathbb{C}_{f(\bullet)}$. Then the algorithm adjusts the up- and down-rejection regions separately to detect as many up- and down-regulated significant DEFs as possible while keeping the estimated FDRs (Eqn. (8)) on both sides under controlled by a user-desired threshold $\Psi$. It tracks the best functions and the corresponding rejection regions separately for detecting the up- and down-regulated DEFs. In our experiments, most of the runtime was spent on computing the basic attributes, and it took almost negligible time to search for the best $f(\bullet)$ once the basic statistics (attributes) were available.

Figure 2:
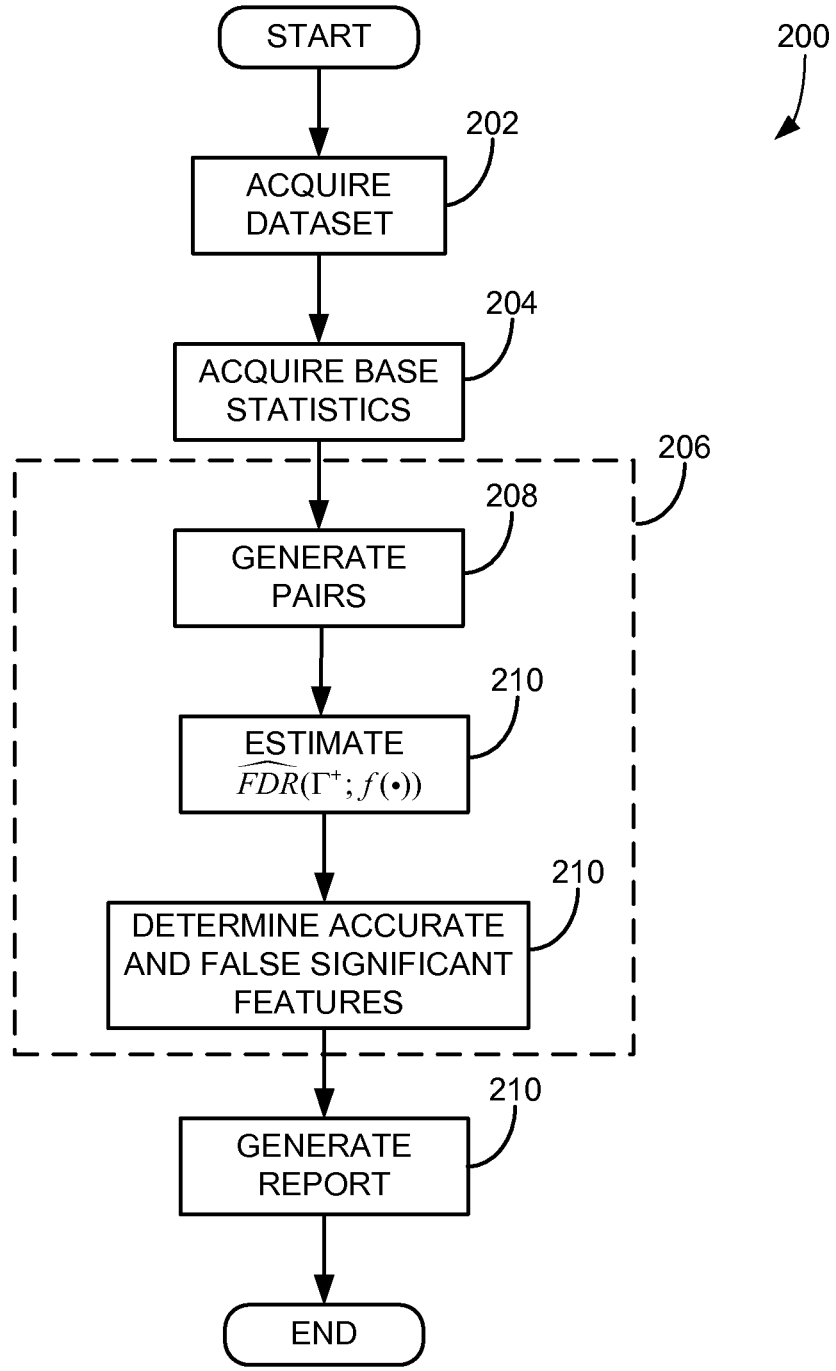
FIG. 2 is a flow chart setting forth examples of steps that may be performed when using a Composite-Cut algorithm in accordance with the present disclosure.

Referring now to FIG. 2 an example of a process for using the Composite-Cut algorithm can be described with respect to a given large dataset, such as may be acquired using a microarray (such as microarray 132 of FIG. 1) to assay biological material. To this end, regardless of the type of dataset or what tools are used to acquire the dataset, or even if the dataset was previously acquired and stored in a memory (such as memory 112 of FIG. 1), the process 200 begins at process block 202 with an acquisition of the dataset, be it from a tool such as a microarray or from memory. Base statistics are acquired at process block 204. For example, the corrected t-test statistic and the corrected ranksum-test statistic can be used.

With the dataset and base statistics in hand, the Composite-Cut algorithm can be performed as generally indicated at 206, for example, using a processor (such as processor or CPU 106 of FIG. 1), to select significant features, for example, to improve false discovery rates (FDR) in the dataset. Again, as described above, assume that there are K different base statistics $\vec{d}_i = [d_i^1, d_i^2, \ldots, d_i^K]$ for the i-th feature that were obtained at process block 204 for every feature in the dataset acquired at process block 202. As will be further detailed, a transformation $f(\bullet)$ will be applied that will be determined in implementation to obtain a Composite-Index, as $\mathbb{C} = \{c_i = f(\vec{d}_i)\}_{i=1,\ldots,M}$.

In calling the positive significant features, the Composite-Cut algorithm, generally designated at 206, can examine all possible transformations $f^+(\bullet)$ and cutoff $\tau$ at a certain degree of granularity to find one combination that identifies the maximal number of significant features and satisfies the FDR constraint. Specifically, at process block 208, a set of transformations $f^+(\bullet)$ may be generated to provide enough coverage on the search space. As will be described in further detail below, for each transformation $f^+(\bullet)$, a positive threshold $\tau$ can be found that yields the largest number of positive significant features (i.e., $D(\Gamma^+ = (\tau, \infty), f^+(\bullet)))$ satisfying $FDR(\Gamma^+, f^+(\bullet)) < \Psi$. An $f^+(\bullet)$ is called desirable (for example, desirable may include optimal), if the number of positive significant features identified under this condition is the largest among all possible transformations.

Figure 3A:
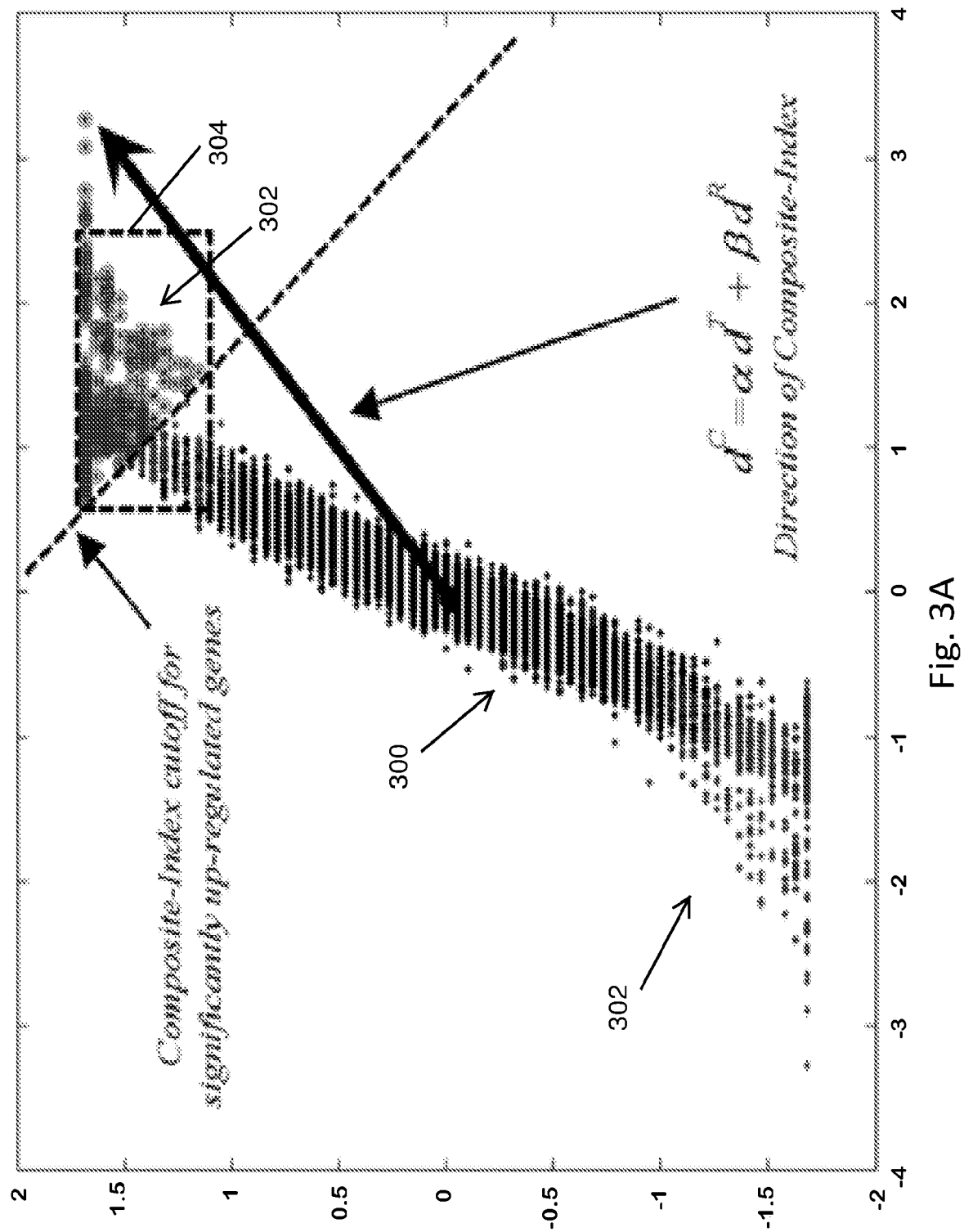
FIG. 3A is a graph illustrating how the Composite-Cut algorithm calls significantly up-regulated features.
Figure 3B:
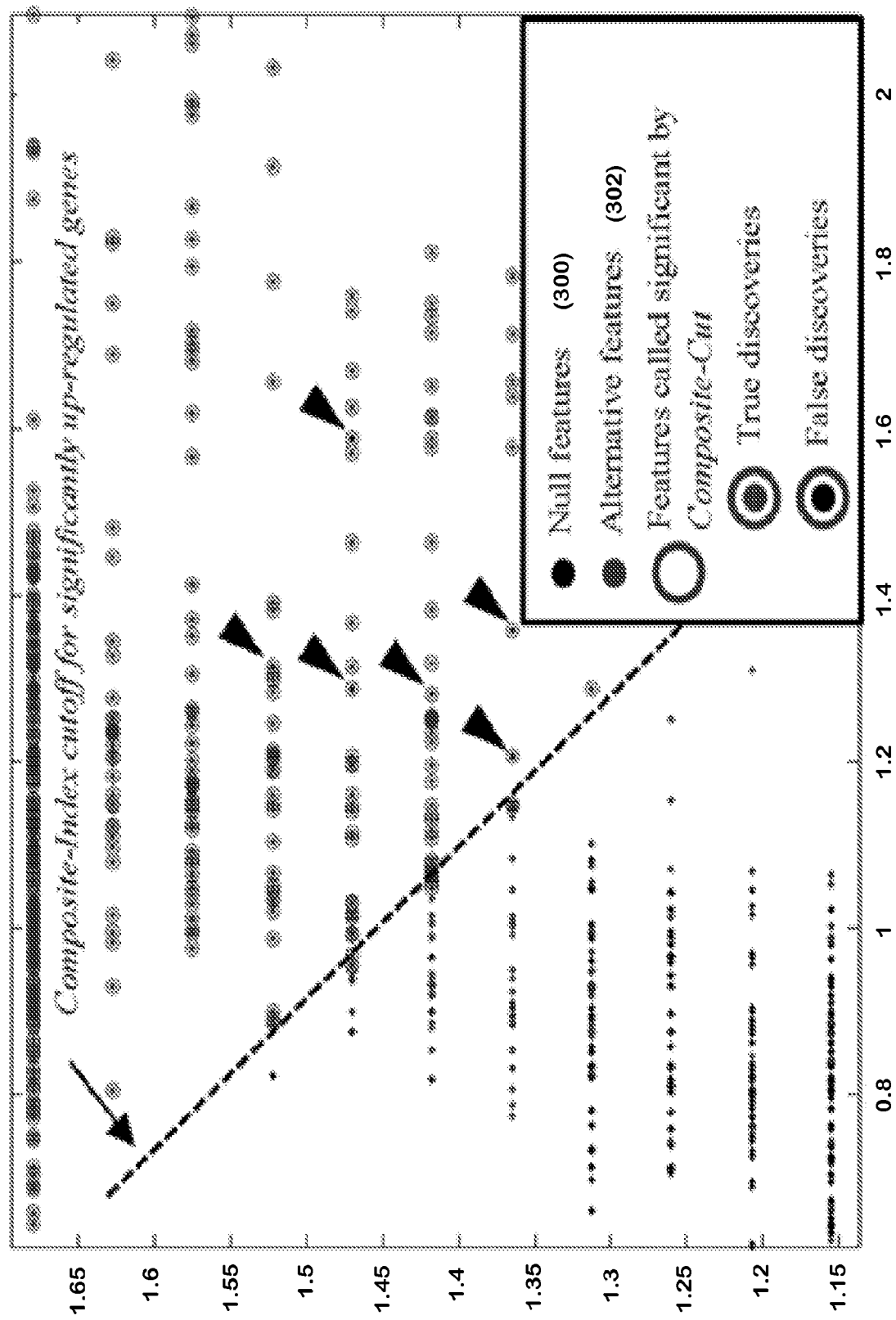
FIG. 3B is a magnification of a portion of the graph of FIG. 3A.

For example, FIGS. 3A and 3B illustrate how Composite-Cut identifies positive significant features. Specifically, to create FIGS. 3A and 3B, a dataset was simulated in the way described below with respect to the "Simulation Test". The black dots 300 represent true null features, and the gray dots 302 represent true alternative features. The x-axis and y-axis indicate the corrected t-statistic $\{d_i^T\}$ and the corrected ranksum-statistic $\{d_i^R\}$, respectively. As such, FIG. 3A provides an overview that visualizes the data distribution, the direction of Composite-Index with coefficients $\langle w_1, w_2 \rangle$ as a vector, and the Composite-Index cutoff for significantly up-regulated genes as a dash line, respectively. The cutoff line separates the whole area into the "Significant" and "Not Significant" regions. Those falling into the "Significant" region are identified by Composite-Cut as significantly up-regulated features. FIG. 3B provides an expanded view of region 304 in FIG. 3A. The arrow heads mark several false discoveries.

At process block 210, to evaluate the pairs generated at process block 208, FDR ($\Gamma^+, f^+(\bullet)$) is estimated using eqn. (2~5).

The FDR of the negative tail can be estimated in a similar way.

Therefore, an algorithm is provided that combines multiple statistical tests to formulate FDR control as an optimization problem. The implementation may assume features are independent from each other and use multiple statistics for each feature to increase the chance of detecting features that behave differentially between conditions. To the latter point, the power of the algorithm treating features independently to increase the ability to detect features under various conditions can be illustrated by way of examples and experiments. As such, as will be described in further detail below with respect to some non-limiting examples, a report may be generated at process block 212 that synthesizes various information, including multiple base statistics, to determine significant features from a dataset, including determining significant features that were previously unknown or unrecognized as being significant.

Experiments

A set of experiments were carried out to compare Composite-Cut with the BH approach, the Storey approach, SAM (v4.0), and miFDR. In these comparisons, 4 approaches were combined with 2 base statistical tests to form eight settings for controlling FDR: (1) BH-t: BH with the t-test, (2) BH-r: BH with the ranksum-test, (3) Storey-t: Storey with the t-test, (4) Storey-r: Storey with the ranksum-test, (5) SAM$^T$-SAM with the corrected t-test, (6) SAM$^R$-SAM with the corrected ranksum-test, (7) miFDR-T: miFDR with the corrected t-test and (8) miFDR-R: miFDR with the corrected ranksum-test. Including Composite-Cut, nine settings for controlling FDR were compared.

Simulation Test

The replicates in the normal group (20 samples) of a real microarray dataset GDS2855 were used. as the null hypotheses in our simulation test so that the null hypotheses have similar complexity to those in reality. GDS2855 contains 22645 probesets, i.e., each of our simulated datasets contains 22645 null hypotheses. First all features in the whole normal group were scaled to have a unit variance so that the value ranges of the null hypotheses are comparable to those of the alternative hypotheses simulated as below. 16 replicates from the normal group of GDS2855 were randomly sampled and divided evenly into two groups. Then 1000 alternative hypotheses (500 positive alternatives and 500 negative alternatives) were simulated following various distributions in Table 1.

TABLE 1

The distributions of simulated hypotheses.

| Feature set | Feature number | Distribution in the 1$^{st}$ Group | Distribution in the 2$^{nd}$ Group |
|---|---|---|---|
| 1 Null | 22645 | Derived from GDS2855 | Derived from GDS2855 |
| 2 Alternative | 30% of all alternatives | 0.5 × U(−0.5, 0.5) + 0.5 × U(−1.5, 1.5) | 0.5 × U(0.4, 1.4) + 0.5 × U(1.2, 4.2) |
| 3 | 5% | U(−1.5, 1.5) | U(1.2, 4.2) |
| 4 | 5% | U(−0.5, 0.5) | U(0.5, 1.5) |
| 5 | 10% | N(0, 1) | N(2.95, 1.5) |
| 6 | 30% | 0.5 × U(−0.5, 0.5) + 0.5 × U(−1.5, 1.5) | 0.5 × U(−1.4, −0.4) + 0.5 × U(−4.2, −1.2) |
| 7 | 5% | U(−1.5, 1.5) | U(−4.2, −1.2) |
| 8 | 5% | U(−0.5, 0.5) | U(−1.5, −0.5) |
| 9 | 10% | N(0, 1) | N(−2.95, 1.5) |

With respect to Table 1, N(μ, σ) stands for the normal distribution with mean μ and standard deviation σ. U(a, b) stands for the uniform distribution in range [a, b]. The null distributions were derived from the control data of real microarray dataset GDS2855.

The distributions of alternative hypotheses were designed to be complex, and some of them are mixtures of different distributions. This setup allows testing of different FDR controlling methods more thoroughly. Moreover, the distributions of features were designed to be symmetric in the positive and negative sides because the main goal here is to demonstrate the benefits of considering multiple base statistics.

The simulation test was run 1000 times. In each simulation run, the target FDR was increased from 0.01 to 0.1 at the step of 0.01, and each of the nine FDR controlling settings identified and reported significant features at every target FDR level. The results are averaged and summarized in FIGS. 4A, 4B, and 4C, which compares Composite-Cut with BH-t, BH-r, Storey-t, Storey-r, SAM-T, SAM-R, miFDR-T, and miFDR-R.

Figure 4A:
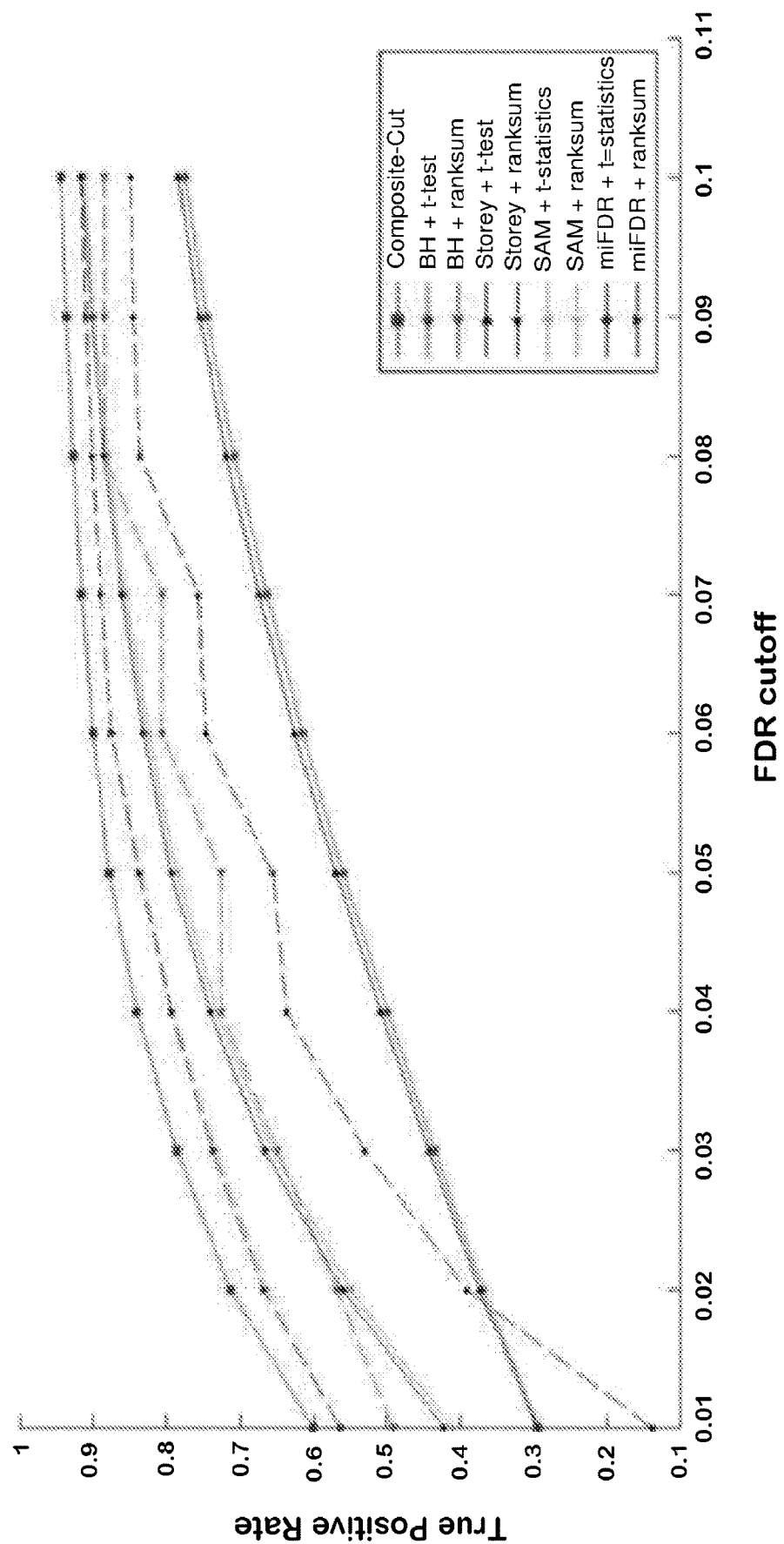
FIG. 4A is a graph showing true positive rates in the target FDR range of [0.01, 0.1].
Figure 4B:
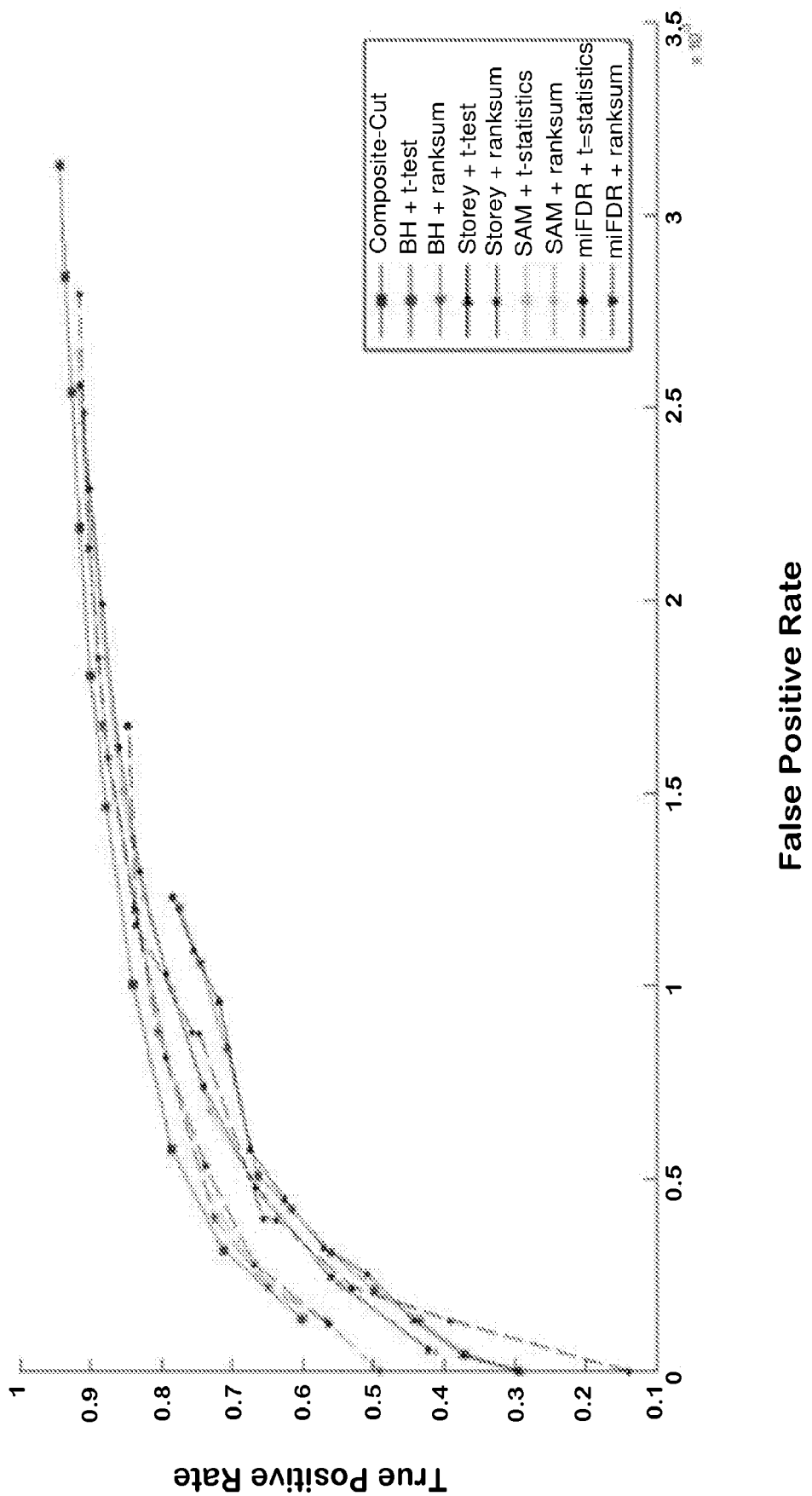
FIG. 4B is a graph of the results of FIG. 4A converted into the ROC curves.
Figure 4C:
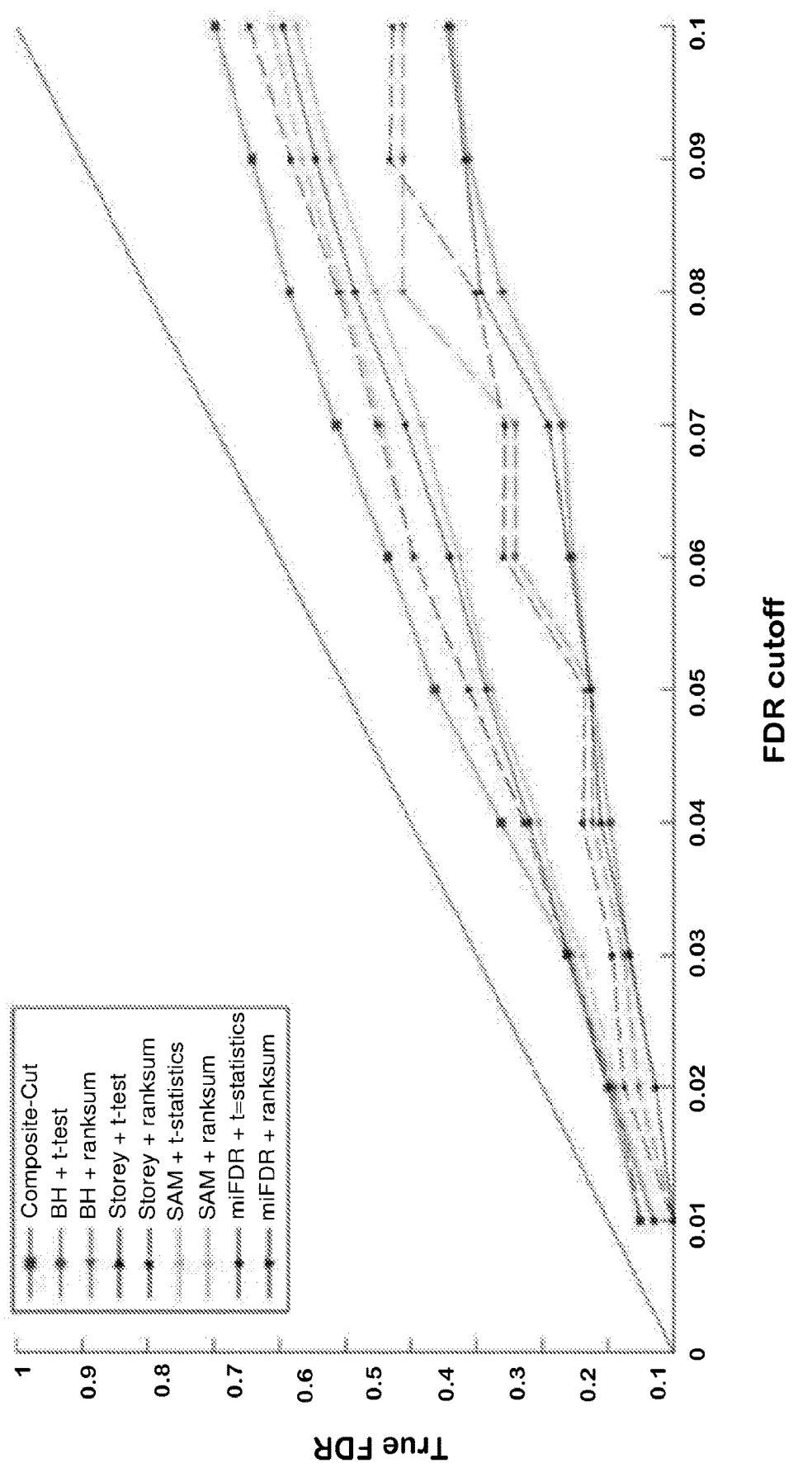
FIG. 4C is a graph showing that the true FDRs are well bounded by the FDR cutoffs, indicating Composite-Cut does not over-estimate FDR.

In particular, FIG. 4A shows that Composite-Cut was capable of identifying more true alternatives than other methods at the same FDR levels. The results were converted into the Receiver-Operating-Characteristic (ROC) curves (true positive rates vs. false positive rates) in FIG. 4B, which confirm from another viewpoint that Composite-Cut performed the best and it is beneficial to integrate multiple base statistics in identifying significant features. FIG. 4C shows that the true FDRs are bounded by the corresponding FDR cutoff levels. Different numbers (20, 200, 500, 2000 and 4000) of alternative hypotheses were also tried, and the results confirmed the supreme performance of Composite-Cut.

Another simulation test showed the value of integrating multiple attributes to detect DEFs compared the Composite-Cut (referred to in this test as Discriminant-Cut or DC) with thirteen other RNA-seq differential expression analysis methods including baySeq (Hardcastle, T. and Kelly, K. (2010) baySeq: Empirical Bayesian methods for identifying differential expression in sequence count data. *BMC bioinformatics*, 11, 1-14), DESeq (Anders, S. and Huber, W. (2010) Differential expression analysis for sequence count data. *Genome biology*, 11, R106), EBSeq (Leng, N., Dawson, J. A., Thomson, J. A., Ruotti, V., Rissman, A. I., Smits, B. M. G., Haag, J. D., Gould, M. N., Stewart, R. M. and Kendziorski, C. (2013) EBSeq: an empirical Bayes hierarchical model for inference in RNA-seq experiments. *Bioinformatics*, 29, 1035-1043), edgeR (Robinson, M. D., McCarthy, D. J. and Smyth, G. K. (2010) edgeR: a Bioconductor package for differential expression analysis of digital gene expression data. *Bioinformatics*, 26, 139-140), NBPSeq (Di, Y., Schafer, D. W., Cumbie, J. S. and Chang, J. H. (2011) The NBP Negative Binomial Model for Assessing Differential Gene Expression from RNA-Seq. *Statistical applications in genetics and molecular biology*, 10, 1-28), SAMseq (Li, J. and Tibshirani, R. (2013) Finding consistent patterns: a nonparametric approach for identifying differential expression in RNA-Seq data. *Statistical methods in medical research*, 22, 519-536), ShrinkSeq (Van De Wiel, M. A., Leday, G. G., Pardo, L., Rue, H., Van Der Vaart, A. W. and Van Wieringen, W. N. (2013) Bayesian analysis of RNA sequencing data by estimating multiple shrinkage priors. *Biostatistics*, 14, 113-128), TSPM (Auer, P. L. and Doerge, R. W. (2011) A Two-Stage Poisson Model for Testing RNA-Seq Data. *Statistical applications in genetics and molecular biology*, 10), voom (Law, C. W., Chen, Y., Shi, W. and Smyth, G. K. (2014) voom: Precision weights unlock linear model analysis tools for RNA-seq read counts. *Genome biology*, 15, R29), limma (Smyth, G. K. (2004) Linear models and empirical bayes methods for assessing differential expression in microarray experiments. *Statistical applications in genetics and molecular biology*, 3, Article3)+ vst (in DESeq package), PoissonSeq (Li, J., Witten, D. M., Johnstone, I. M. and Tibshirani, R. (2012) Normalization, testing, and false discovery rate estimation for RNA-sequencing data. *Biostatistics*, 13, 523-538), DESeq2 (Love, M. I., Huber, W. and Anders, S. (2014) Moderated estimation of fold change and dispersion for RNA-seq data with DESeq2. *Genome biology*, 15, 550), and ODP (Storey, J. D. (2007) The optimal discovery procedure: a new approach to simultaneous significance testing. *Journal of the Royal Statistical Society: Series B (Statistical Methodology)*, 69, 347-368). DC was allowed to use up to three representative basic attributes: (1) $s^T$—the moderated t-statistic from voom, (2) $s^R$—the corrected ranksum statistic from SAM, and (3) $s^{NB}$—the Wald statistic for NB-based differential expression test from DESeq2. This produced seven DC versions: $DC^T$ (DC using $s^T$), $DC^R$ (DC using $s^R$), $DC^{NB}$ (Dc using $s^{NB}$), $DC^{T+R}$ (DC using $s^T$ and $s^R$), $DC^{R+NB}$ (DC using $s^R$ and $s^{NB}$), $DC^{T+NB}$ (DC using $s^T$ and $s^{NB}$), and $DC^{T+R+NB}$ (DC using $s^T$, $s^R$ and $s^{NB}$). Note that different DC versions use the same FDR estimation approach, which allows assessment of the advantages of combining multiple basic attributes. Different FDR control methods are used by some of those thirteen existing DEF detection methods, and are included to compare the overall performances.

Test datasets were simulated based on a real RNA-seq dataset—the Montgomery dataset (Downloaded from http://bioinf.wehi.edu.au/PublicDatasets/ as of Apr. 15, 2015), which contains the read-counts of 25702 genes in 60 biological replicates. Genes with extremely low expression profiles (read counts below 10 in more than half of the replicates) were removed first. For each of the remaining 11573 genes, it was decided whether its read counts could be better modeled by a negative binomial (NB) distribution or a Gaussian mixture model (GMM) in the following way. The NB and GMM distribution were estimated by using DESeq2 implemented in R and the statistics toolbox of MATLAB R2013a, respectively. The most proper number of components in a GMM was decided based on the Bayesian Information Criterion. The GMMs of ~44%, ~50%, and ~6% genes contained 1, 2, and 3 components, respectively. Then, for each gene, the correlation between the histograms of its read-counts and the corresponding fitted NB/GMM was calculated to decide which distribution was a better fit. The GMMs were truncated at zeros because read counts should be non-negative. The distributions of about 63.5% and 36.5% of genes can be better represented by GMM and NB, respectively. This example clearly shows that real data distributions are indeed complex.

In each simulation test, N read-counts were simulated for every gene according to the distribution (either NB or GMM) chosen in the above way, and the simulated read-counts were randomly divided into two equal-size groups to obtain true non-DEFs. The simulation of a gene was repeated until its logarithmic fold-change was not larger than $4.5\sigma_N$, where $\sigma_N$ is the standard deviation of the logarithmic fold-change between two N-sample groups randomly chosen from the Montgomery dataset. The $4.5\sigma_N$ fold-change threshold was chosen because we observed in the Montgomery dataset that the expected number of fold-changes higher than $4.5\sigma_N$ is below 0.05, which rounds up to 0. Lowering the threshold to $4\sigma_N$ raised the expected number to 0.3, which rounds up to 1. Then $G_b^a$ genes (a and b are the numbers of up- and down-regulated genes, respectively) were randomly made as true DEFs in the following way. For each of the chosen genes, one of its groups was multiplied or divided by a factor uniformly sampled between 1.5 and 3.0 to provide a reasonable wide range of differences in expression. Finally, all simulated values were rounded to their nearest integers.

A series of simulation tests were conducted under 20 different settings: 5 different sample sizes (N=8, 10, 12, 16, and 20)×4 different sizes/distributions of true DEFs ($G_{400}^{400}$, $G_{500}^{500}$, $G_{600}^{600}$, and $G_0^{1000}$). At each of the above simulation settings, the test was run 100 times and the numbers of the detected DEFs and the actual FDRs recorded at two typical target FDR levels (0.01 and 0.05). All comparisons focused on two key performance factors: 1) the effectiveness of FDR control, namely whether the real FDR is effectively bounded by the desired FDR; and 2) the detection power, namely the ability to detect as many significant DEFs as possible without violating (1).

The overall performance of DC was better than other methods. Voom and vst/limma in general performed similarly better than other non-DC methods. All DC versions were able to effectively control the FDR. EdgeR, NBPSeq, EBSeq, ShrinkSeq, and baySeq significantly underestimated their FDRs although they detected much more DEFs. In addition, DESeq2 also significantly underestimated the FDR. Although both SAMSeq and DESeq were able to well control the FDR, they were relatively more conservative. ShrinkSeq is substantially slower than other methods. Among those able to effectively control the FDR, $DC^{T+R+NB}$ performed the best. At FDR<0.01, $DC^{T+R+NB}$ on average detected 271.30 DEFs, which was significantly better (paired t-test p-value=1.36e-79) than the 202.85 DEFs detected by the best non-DC method (vst/limma). At FDR<0.05, $DC^{T+R+NB}$ on average detected 460.17 DEFs, which was significantly better (p-value=5.36e-77) than the 400.44 DEFs detected by the best non-DC method (vst/limma).

In this comparison, a method is deemed to have a reasonable FDR controlling capability if its average true FDR does not exceed 20% of the target cutoff, for example, 0.05×(1+20%)=0.06 for the target FDR<0.05. Six methods (ShrinkSeq, edgeR, DESeq2, EBSeq, baySeq and NBPSeq) consistently failed to meet this criterion under all simulation test settings. Therefore they were excluded from the following comparison which focuses on discussing $DC^{T+R+NB}$, PoissonSeq, voom, vst/limma, DESeq, SAMSeq, ODP and TSPM. At FDR<0.05, $DC^{T+R+NB}$ consistently outperformed other methods under various settings. Both vst/limma and voom performed similarly better than other non-DC methods across a wide range of DEF sizes (e.g., $G_{400}^{400}$, $G_{500}^{500}$ and $G_{600}^{600}$). However, their performances dropped remarkably when the sizes of the up- and down-regulated true DEFs were extremely unbalanced (e.g., $G_0^{1000}$). SAMSeq required a relatively larger sample size to work well, and was not significantly affected by the skewed distribution of true DEFs when the sample set was large enough. TSPM worked well when the sample size was relatively larger and the sizes of up- and down-regulated true DEFs were compatible. DESeq in general was more conservative but dramatically underestimated the FDR when the sample set was small.

When the sample size was decreased, all methods detected less DEFs, and it was more challenging to control the FDR, especially when a more stringent target FDR was imposed. Small sample size makes it more difficult not only for parametric approaches to reliably estimate the parameters of the assumed distributions but also for permutation-based approaches to generate enough permutations to approximate the null distribution well. For example, when N=8 and the target FDR<0.01, all methods failed to control the FDR. $DC^{T+R+NB}$ on average detected less than 20 DEFs, and one single false positive alone would increase its true FDR by 0.05, which is much higher than the target FDR cutoff.

Comparing the results of different DC versions (Table 2) shows the benefit of integrating multiple basic attributes in detecting DEFs. Even though some individual attributes alone may be inferior to other attributes in detecting DEFs, they can indeed provide substantial enhancements to other attributes. For example, DCR performed significantly worse than both $DC^T$ and $DC^{NB}$ due to the aforementioned shortcomings of the ranksum statistic. Adding $s^R$ to $s^{NB}$ significantly improved the results by 8.10% (p-value=9.48e-38) at FDR<0.01 and by 4.11% (p-value=3.85e-40) at FDR<0.05. Results of different sample sizes confirm the above observation. For example, Table 3 shows that $DC^{T+R+NB}$ consistently outperformed single-attribute DC versions across different sample sizes at FDR<0.05 and $G\_500^\ 500$. When N=8, $DC^{T+R+NB}$ on average detected 11.1% and 97.3% more DEFs than DCT and $DC^{NB}$, respectively.

Grouping the DEFs detected by $DC^T$, DCR, $DC^{NB}$, and $DC^{T+R+NB}$ accordingly to their distribution categories (Table 4), it is observed that integrating multiple basic attributes helps to detect DEFs across the whole distribution spectrum. Interestingly, $DC^T$ on average detected more DEFs governed by NB distributions than $DC^{NB}$, which to some extent resonates with the idea of voom, i.e., it is sometimes more important to model the mean-variance relationship correctly than to design the exact distribution of read-counts.

TABLE 2

Compares the simulation test results (N = 16; $G_{500}^{500}$) of different DC versions.

| baseline | Target FDR | Add $s^T$ | Add $s^R$ | Add $s^{NB}$ | Use $s^T$, $s^R$, and $s^{NB}$ |
|---|---|---|---|---|---|
| Use $s^T$ alone | 0.01 | — | +2.34% (1.06e-21) | +3.88% (2.76e-33) | +5.26% (4.22e-43) |
| | 0.05 | — | +1.05% (4.06e-19) | +5.13% (1.40e-40) | +5.94% (2.67e-44) |
| Use $s^R$ alone | 0.01 | +517% (4.23e-61) | — | +506% (1.73e-60) | +534% (1.37e-62) |
| | 0.05 | +41.8% (2.02e-88) | — | +44.8% (1.67e-89) | +48.7% (2.92e-94) |
| Use $s^{NB}$ alone | 0.01 | +11.7% (1.03e-51) | +8.10% (9.48e-38) | — | +13.2% (1.97e-56) |
| | 0.05 | +6.07% (1.57e-46) | +4.11% (3.85e-40) | — | +6.89% (1.97e-50) |

TABLE 3

Compares the simulation test results (FDR < 0.05, $G_{500}^{500}$) of different sample sizes.

| | Sample size | | | | |
|---|---|---|---|---|---|
| Methods | N = 20 (10 vs. 10) | N = 16 (8 vs. 8) | N = 12 (6 vs. 6) | N = 10 (5 vs. 5) | N = 8 (4 vs. 4) |
| $DC^T$ | 551.61 (2.89e-58) | 434.36 (2.67e-44) | 265.36 (2.19e-40) | 146.96 (1.85e-29) | 36.63 (1.25e-11) |
| $DC^R$ | 485.47 (1.48e-91) | 309.44 (2.92e-94) | — | — | — |

TABLE 3-continued

Compares the simulation test results (FDR < 0.05, $G_{500}^{500}$) of different sample sizes.

| Methods | Sample size | | | | |
|---|---|---|---|---|---|
| | N = 20 (10 vs. 10) | N = 16 (8 vs. 8) | N = 12 (6 vs. 6) | N = 10 (5 vs. 5) | N = 8 (4 vs. 4) |
| $DC^{NB}$ | 570.34 (1.55e−50) | 430.51 (1.97e−50) | 237.63 (6.15e−61) | 108.87 (5.19e−57) | 16.43 (3.11e−37) |
| $DC^{T+R+NB}$ | 590.39 | 460.17 | 283.10 | 162.11 | 42.05 |

TABLE 4

Compares the average numbers of DEFs identified in different distribution categories.

| Detected by | Total | NB | Gaussian | GMM (2 or 3 components) |
|---|---|---|---|---|
| $DC^T$ | 434.36 (2.67e−44) | 184.02 (3.17e−30) | 91.77 (3.19e−36) | 158.57 (2.78e−31) |
| $DC^R$ | 309.44 (2.92e−94) | 153.85 (8.78e−73) | 67.39 (6.57e−69) | 88.20 (6.39e−88) |
| $DC^{NB}$ | 430.51 (1.97e−50) | 178.85 (3.44e−45) | 91.48 (3.52e−31) | 160.18 (6.51e−32) |
| $DC^{T+R+NB}$ | 460.17 | 192.00 | 97.54 | 170.63 |

None of the basic attributes consistently performed better than other basic attributes in our simulation tests, which resonates with the idea of utilizing multiple attributes. For example, when N=16 and $G_{600}^{600}$, $DC^T$ on average detected more DEFs than $DC^{NB}$ (373.96 vs. 361.25) at FDR<0.01, but performed worse than $DC^{NB}$ (551.61 vs. 570.34) at FDR<0.05. Moreover, at FDR<0.05, $DC^T$ outperformed $DC^{NB}$ on datasets when the sample size was relatively small (e.g., N=8, 10 and 12 in Table 3) while $DC^{NB}$ outperformed $DC^T$ when the sample size was larger (e.g., N=20 in Table 3). Interestingly, although $DC^R$ underperformed both DCT and DCNB under most settings, $DC^R$ outperformed them when N=20, $G_0^{1000}$ and target FDR<0.05 (DEFs: 583.04 by DCR vs. 556.54 by DCT and 575.61 by $DC^{NB}$).

The simulated test results also show that non-parametric processes, which directly use attributes, can be more effective in controlling FDR than those converting attributes into p-values parametrically when data distributions are complex and there are enough samples. For instance, DESeq2 was not able to well control the FDR. However, $DC^{NB}$ was able to control the FDR even though it used the statistics calculated by DESeq2. DESeq2 calculates the p-value of each statistic and then applies the BH approach to identify DEFs. Nevertheless, DCNB implements the Storey framework with a non-parametric setup to estimate the FDR. Since the BH approach is, in general, more conservative than the Storey approach, we suspect that the p-values calculated by DESeq2 might not be accurate enough because the real data distributions are far more complex than what assumed by DESeq2. In this simulation, ~36% of genes were sampled from NB distributions, whose parameters were estimated by DESeq2. However, the other ~64% genes were sampled from GMM models, which could significantly affect the performances of the NB-based parametric approaches (e.g., DESeq2).

Applications

The above-described systems and methods can be applied to a variety of datasets and applications. One non-limiting example of a dataset for which the present disclosure is particularly well suited includes gene expression datasets. To this end, the present disclosure may be used to analyze DNA microarray datasets.

The above FDR control settings were compared in analyzing ten Microarray datasets obtained from Gene Expression Omnibus (GEO, http://www.ncbi.nlm.nih.gov/geo/): GDS2874, GDS3395, GDS2878, GDS2647, GDS2884, GDS3465, GDS2470, GDS2491, GSE28462, and GSE20910. Each of the foregoing is incorporated herein by reference in its entirety and more information about these datasets is provided in Table 5.

TABLE 5

GEO datasets

| Dataset | Group 1 (sample #) vs. Group 2 (sample #) | Feature # |
|---|---|---|
| GDS2470 | Normal (5) vs. Neural tube defect (4) | 54675 |
| GDS2491 | Control (4) vs. Cigarette smoking (5) | 54675 |
| GDS2647 | Control/wild type (4) vs. Control/ RAG null mutant (4) | 45101 |
| GDS2874 | Wild type (4) vs. PHGDH null (4) | 45101 |
| GDS2878 | Non-pregnant (7) vs. Pregnant (9) | 45101 |
| GDS2884 | Wild type (8) vs. EMD null (6) | 45101 |
| GDS3395 | Control (7) vs. AQP11 null (9) | 45101 |
| GDS3465 | PPARalpha null/control (4) vs. PPARalpha null/pressure overload (4) | 45101 |
| GSE28462 | Diagnosis ALL bone marrow samples Early (<36 months) relapse (29) vs. Late (>=36 months) relapse (20) | 54675 |
| GSE20910 | Non-Down syndrome (26) vs. Down syndrome (23) | 54675 |

All datasets were preprocessed in the same ways as they were done in the original papers (the preprocessed datasets can be downloaded from GEO). The detection results following below in Table 6 show that Composite-Cut was capable of detecting more significant features than other methods at FDR<0.05.

TABLE 6

Comparison of Composite-Cut with traditional methods at FDR < 0.05 on various GEO datasets.

| Dataset | Composite-Cut | FDR control | | | | | | | |
|---|---|---|---|---|---|---|---|---|---|
| | | miFDR-T | miFDR-R | SAM-T | SAM-R | Storey-t | Storey-r | BH-t | BH-r |
| GDS2470 | 284 | 99 | 0 | 43 | 0 | 4 | 0 | 4 | 0 |
| GDS2491 | 14 | 7 | 0 | 6 | 0 | 1 | 0 | 2 | 0 |

TABLE 6-continued

Comparison of Composite-Cut with traditional methods at FDR < 0.05 on various GEO datasets.

| Dataset | Composite-Cut | FDR control | | | | | | | |
|---|---|---|---|---|---|---|---|---|---|
| | | miFDR-T | miFDR-R | SAM-T | SAM-R | Storey-t | Storey-r | BH-t | BH-r |
| GDS2647 | 434 | 368 | 0 | 323 | 0 | 12 | 0 | 10 | 0 |
| GDS2874 | 66 | 42 | 0 | 24 | 0 | 1 | 0 | 1 | 0 |
| GDS2878 | 107 | 90 | 0 | 0 | 0 | 0 | 0 | 0 | 0 |
| GDS2884 | 24 | 19 | 0 | 18 | 0 | 6 | 0 | 6 | 0 |
| GDS3395 | 641 | 454 | 387 | 421 | 505 | 98 | 56 | 98 | 210 |
| GDS3465 | 25 | 18 | 0 | 7 | 0 | 13 | 0 | 13 | 0 |
| GSE28462 | 11 | 5 | 4 | 0 | 1 | 0 | 0 | 0 | 0 |
| GSE20910 | 535 | 498 | 221 | 422 | 205 | 1 | 1 | 15 | 26 |

As detailed below, the results of GSE28462 and GSE20910, both of which are related to acute lymphoblastic leukemia (ALL), are used to discuss the biological insights offered by the genes detected by Composite-Cut alone.

GSE28462

Childhood ALL is the most common type of children cancer. ALL children who relapse late (36 months from initial diagnosis) fare better than those who relapse early in treatment. However, the prognoses for these children remain poor. GSE28462 was generated for the purpose of discovering the molecular mechanisms that may play a role in drug resistance and relapse. A comparison was done of the gene expression of the diagnosis samples of 29 ALL children who relapse late with those of 20 ALL children who relapse early. At FDR<0.05, Composite-Cut detected 11 probesets, which is much better than the 2nd and 3rd best performers miFDR-T and miFDR-R that detected 5 and 4 probesets, respectively. Five probesets (211941_s_at, 207593_at, 228424_at, 218764_at, and 202705_at) were identified by Composite-Cut alone, and they were mapped to genes PEBP1, ABCG4, NAALADL1, PKC-L, and CCNB2, respectively.

Three of them (PEBP1, PKC-L, and CCNB2) are closely related to cancer and may have strong effects in the mechanisms contributing to better prognosis in childhood ALL. PEBP1 (also known as RKIP) was up-regulated (1.53 folds) in early relapse ALL children. This gene encodes a protein that inhibits proliferation and transformation of myeloid cells. Analysis of 388 acute myeloid leukemia patients showed that loss of PEBP1 significantly correlated with longer relapse-free survival and overall survival. Hence, PEBP1 can be a favorable prognostic feature in childhood ALL. PKC-L was down-regulated (0.59 folds) in early relapse ALL children. PKC-L is essential for the generation of the suppressive effects of IFN-α on normal and leukemic myeloid bone marrow progenitors. PKC-L can activate a p38 delta mitogen-activated protein kinase cascade that targets CEBPA, which results in regulating human keratinocyte differentiation. Interestingly, it was reported that human cancer cells can be induced by CEBPA to transdifferentiate into seemingly normal cells at high efficiencies. Basically, CEBPA can induce macrophage transdifferentiation of B lymphoma and leukemia cell lines and impair their tumorigenicity. CCNB2 was up-regulated (2.13 folds) in early relapse ALL children. This gene encodes a member of the cyclin protein family and has been found to be up-regulated in human cancers. A study showed that detection of serum circulating CCNB2 mRNA may have clinical potentials in screening and monitoring of metastasis and therapeutic treatments.

The fourth gene ABCG4 was slightly down-regulated in early relapse ALL children. This gene encodes a protein member in the superfamily of ATP-binding cassette transporters and is involved in the transport of cholesterol from cells to lipidated lipoproteins. Low density lipoprotein is one form of cholesterol, which is the main source of artery-clogging plaque. A study showed that a substantial proportion of ALL survivors had an atherogenic low density lipoprotein phenotype, which may explain why survivors of childhood ALL have an increased risk of cardiovascular disease. Its mouse homolog (Abcg4) is highly expressed in bone marrow megakaryocyte progenitors, and ABCG4 deficiency in bone marrow increases platelet count and accelerates atherosclerosis and thrombosis. Therefore, higher ABCG4 expression levels in ALL patients may contribute to better treatment outcomes. No evidence shows that NAALADL1 has been well studied in any biological context.

GSE20910

Figure 5:
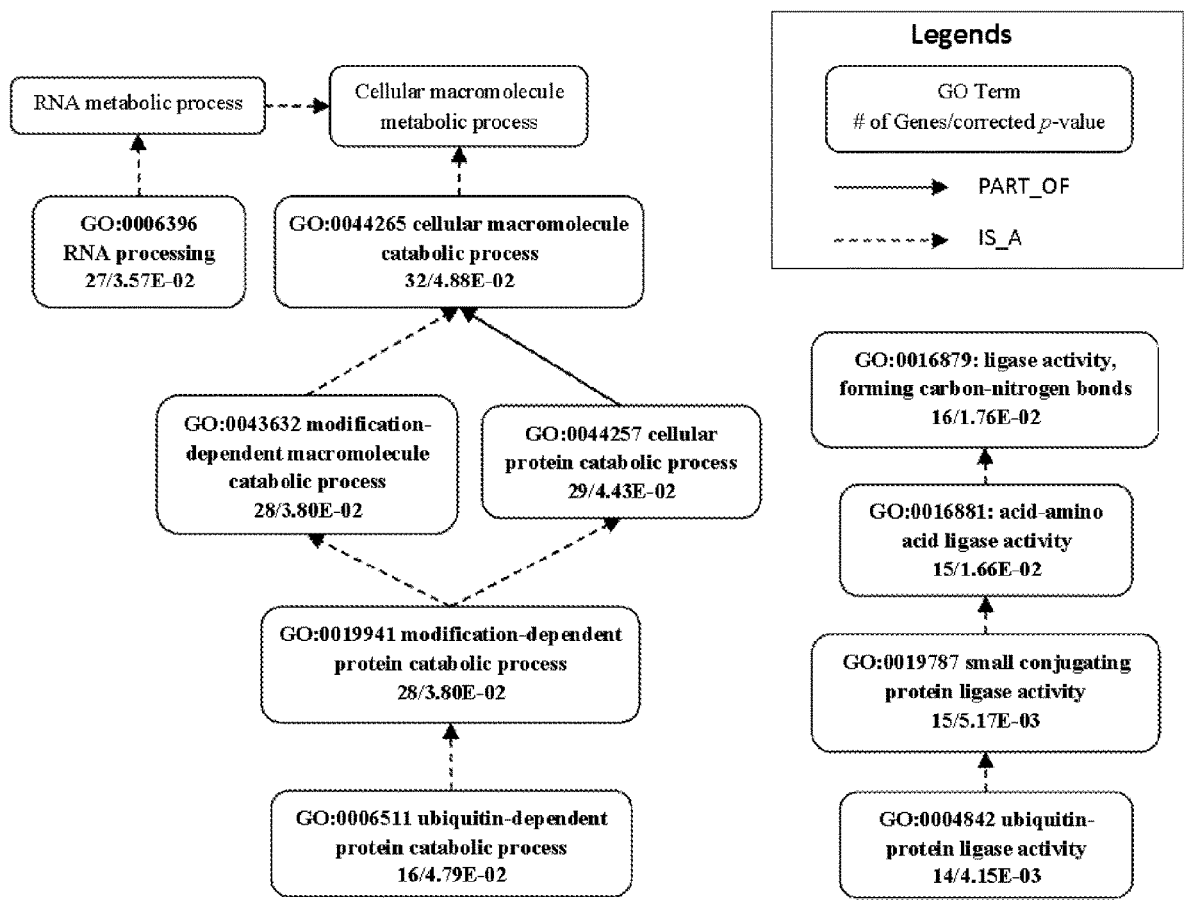
FIG. 5 is a chart showing a Gene Ontology sub-tree that includes 10 enriched GO terms identified by Composite-Cut.

ALL patients with Down syndrome (ALL-DS) have distinct clinical features and significant differences in treatment response and toxicity profiles compared to those without Down syndrome (Non-DS). It has been observed that ALL-DS patients suffered from increased susceptibility to infection, in part attributable to functional impairments in B-cell, T-cell and phagocytic cell function. To investigate the underlying molecular foundations, GSE20910 contains gene expressions extracted from the ficoll-enriched, cryopreserved diagnostic bone marrow samples, which were obtained from 23 ALL-DS patients and 26 Non-DS patients with newly diagnosed B-precursor ALL. At FDR<0.05 (Table 3), Composite-Cut identified 535 probesets, which is 37 more than the 2nd best performer miFDR-T. The probeset list detected by Composite-Cut was submitted to DAVID for Gene Ontology (GO) enrichment analysis, and 11 enriched functional categories (Benjamini p-value <0.05) were identified. The relations between these categories are summarized in FIG. 5.

The GO analysis results of the gene lists identified by Composite-Cut and miFDR-T were compared. In Table 7, GO categories enriched in the gene list identified by Composite-Cut (corrected p-value <0.05).

TABLE 7

GO categories enriched in the gene list identified
by Composite-Cut (corrected p-value < 0.05)

| GO term | Gene count | Corrected p-value | Enriched in the gene list called by other methods (number of genes, corrected p-value) |
|---|---|---|---|
| GO:0019941 - modification-dependent protein catabolic process | 28 | 0.038 | — |
| GO:0016879 - ligase activity, forming carbon-nitrogen bonds | 16 | 0.0176 | $SAM^T$ (13, 0.0444) |
| GO:0044257 - cellular protein catabolic process | 29 | 0.0443 | — |
| GO:0006396 - RNA processing | 27 | 0.0357 | $SAM^T$ (26, 0.0022) |
| GO:0019787 - small conjugating protein ligase activity | 15 | 0.0052 | $SAM^T$ (12, 0.0119) |
| GO:0016881 - acid-amino acid ligase activity | 15 | 0.0166 | $SAM^T$ (12, 0.0412) |
| GO:0006511 - ubiquitin-dependent protein catabolic process | 16 | 0.0479 | — |
| GO:0000166 - nucleotide binding | 78 | 0.004 | $miFDR^T$ (73, 0.0146) $SAM^T$ (62, 0.0053) |
| GO:0004842 - ubiquitin-protein ligase activity | 14 | 0.0042 | $SAM^T$ (12, 0.0079) |
| GO:0043632 - modification-dependent macromolecule catabolic process | 28 | 0.038 | — |
| GO:0044265 - cellular macromolecule catabolic process | 32 | 0.0488 | — |

The last column indicates if a GO category is also enriched in the gene list called by another method, in which the corresponding gene numbers and corrected p-values are provided. More GO categories are enriched in the gene list called by Composite-Cut than in the gene lists called by other methods, as illustrated in Tables 8 and 9 below.

TABLE 8

GO categories enriched in the gene list identified
by miFDR-T (corrected p-value < 0.05)

| GO term | Gene count | Corrected p-value | Enriched in the gene list called by other methods (number of genes, corrected p-value) |
|---|---|---|---|
| GO:0000166 - nucleotide binding | 73 | 0.0146 | Composite-Cut (78, 0.004) $SAM^T$ (62, 0.00533) |
| GO:0006414 - translational elongation | 11 | 0.048 | — |

Although GO:0006414 is not enriched in the gene list called by Composite-Cut, both Composite-Cut and miFDR-T called the same number of genes in this GO category.

TABLE 9

GO categories enriched in the gene list identified
by SAM-T (corrected p-value < 0.05).

| GO term | Gene count | Corrected p-value | Enriched in the gene list called by other methods (number of genes, corrected p-value) |
|---|---|---|---|
| GO:0016879 - ligase activity, forming carbon-nitrogen bonds | 13 | 0.0444 | Composite-Cut (16, 0.0176) |
| GO:0006396 - RNA processing | 26 | 0.0022 | Composite-Cut (27, 0.0357) |
| GO:00197B7 - small conjugating protein ligase activity | 12 | 0.0119 | Composite-Cut (15, 0.0052) |
| GO:0016881 - acid-amino acid ligase activity | 12 | 0.0412 | Composite-Cut (15, 0.0166) |
| GO:0000166 - nucleotide binding | 62 | 0.0053 | Composite-Cut (78, 0.004) $miFDR^T$ (73, 0.0146) |
| GO:0004842 - ubiquitin-protein ligase activity | 12 | 0.0079 | Composite-Cut (14, 0.0042) |

In two finest enriched GO categories (GO:0006511 ubiquitin-dependent protein catabolic process & GO:0004842 ubiquitin-protein ligase activity), Composite-Cut identified 24 genes in total, which is three more than the 21 genes identified by miFDR-T. These three genes are UBE2H, UBR1, and TRIP12, which were up-regulated in ALL-DS patients with 1.59, 1.56, and 1.73-folds, respectively. They are involved in the Adaptive Immune System (www.ncbi.nlm.nih.gov/biosystems/366160), which indicates that the adaptive immune system is elevated in ALL-DS patients. This is consistent with the fact that ALL-DS individuals in general experience a higher frequency of infections. In addition, it was shown that TRIP12 works with UBR5 to suppress spreading of chromatin ubiquitylation at damaged chromosomes, which is vital for the homeostasis of ubiquitin-controlled events after DNA breakage and can be subverted during tumorigenesis. Interestingly, mutations in UBR1 have been associated with Johanson-Blizzard syndrome (www.ncbi.nlm.nih.gov/gene/197131) that shares several symptoms with Down syndrome, such as mental retardation and poor physical growth.

Analyzing the TCGA Acute Myeloid Leukemia mRNA-Seq Gene Expression Dataset

Composite-Cut was further compared against eight other FDR control settings on an Acute Myeloid Leukemia (AML) mRNA-seq dataset (V2) downloaded from The Cancer Genome Atlas (TCGA: http://cancergenome.nih.gov/) as of May 22, 2013. The gene expression signals pre-computed by TCGA were used in this analysis. A relatively large portion of patients in this cohort had an intermediate/normal cytogenetic risk. Some of them did well with chemotherapeutic consolidation while others had a very poor outcome. Recent studies have discovered that AML biomarkers (e.g., mutations in FLT3, IDH, NPM, and several other genes) provide prognostic information for patients in this risk category. Nevertheless, none of the current classification schemes is entirely accurate. To identify gene activities relevant to the pathogenesis of AML, which may ultimately lead to better therapeutic approaches, we decided to analyze the gene expression data of deceased patients in the intermediate/normal cytogenetic risk category so that the survival time of each patient was known. Patients with prior diagnosis history were filtered out to avoid the effects of prior malignancies, and white (Caucasian) patients were focused on because other races make up a tiny portion in this dataset.

Finally, got two groups of patients were gathered: (a) the Short group—18 patients survived no more than 244 days and (2) the Long group—15 patients survived at least 335 days. Patients were arranged in such way that the Long group survived at least 3 months longer than the Short group and we have relatively balanced numbers of patients in these two groups.

Composite-Cut, BH-t, BH-r, Storey-t, Story-r, SAM-T, SAM-R, miFDR-T, and miFDR-R were applied to identify DEGs—genes that are significantly differentially expressed between the Short and Long groups. At FDR<0.05, Composite-Cut identified 4 genes, while the other FDR control settings identified none. These four genes were: PPFIA1 (up-regulated in the Long group with 1.30 folds), STX6 (up-regulated in the Long group with 1.41 folds), ZFYVE16 (up-regulated in the Long group with 1.81 folds) and TSSC1 (down-regulated in the Short group with 1.38 folds). The possibility of building a classifier to separate the Long and Short groups by the expression levels of PPFIA1, ZFYVE16, TSSC1 and STX6 was investigated. Applying the Bayes Network classifier (Bouckaert, R., Bayesian network classifiers in Weka, 2004.), an average accuracy of 87.88 percent was achieved in 10-fold cross-validation. The results of the following analyses suggest that these DEGs may be valuable prognostic biomarkers and should be interesting subjects of future investigation in the context of AML. Two of them (STX6 and ZFYVE16) are clearly biologically relevant to AML, and TSSC1 has not been well studied in any biological context, which can make it even more interesting.

This mRNA-seq dataset comes with the clinical information of patients, which contains molecular abnormality test results (i.e., the responses of patients to several AML biomarker tests). Most patients were tested for six mutations: (1) FLT3 Mutation, (2) IDH1 R132, (3) IDH1 R140, (4) IDH1 R172, (5) Activating RAS and (6) NPMc, which are known to be prognostic markers for AML patients. It was wondered if there exists any relationship between those four DEGs and these molecular abnormalities. Two trivial abnormalities IDH1 R172 and Activating RAS were removed from these analyses because the responses of all chosen patients to these two markers were negative. Chi-square test results, as provided in Table 10, indicate that (a) the dependency between survival time and FLT3 Mutation is marginally significant (p-value=0.053); and (b) the dependency between survival time and each of the rest three abnormalities is not significant.

TABLE 10

Dependency between survival time (Short or Long) and molecular abnormalities using Chi-square independent test

| Abnormality | # of Positives | # of Negatives | Chi-square p-value |
|---|---|---|---|
| FLT3 Mutation | 10 | 23 | 0.052821 |
| IDH1 R132 | 3 | 30 | 0.658332 |
| IDH1 R140 | 5 | 28 | 0.478247 |
| NPMc | 11 | 22 | 1.000000 |

Hence, the prognostic values of the binary responses to these mutation biomarkers were very limited for patients in this cohort. Survival analysis results using Cox proportional-hazards regression confirmed this conclusion, as illustrated in Table 11. That is, the results indicate that the prognostic values of the binary responses to these mutation biomarkers are very limited for the patients in this example.

TABLE 11

Cox proportional-hazards regression survival analysis using each individual molecular abnormality as predictor (Positive = 1 and Negative = 0) and the survival time as dependent variable

| Abnormality | coefficient | Log-likelihood | p-value |
|---|---|---|---|
| FLT3 Mutation | 0.360891 | −85.220458 | 0.366192 |
| IDH1 R132 | −0.698752 | −85.109740 | 0.308291 |
| IDH1 R140 | −0.290025 | −85.443435 | 0.542681 |
| NPMc | −0.550600 | −84.643345 | 0.160366 |

On the contrary, as illustrated in Table 12, the continuous expression levels of PPFIA1, ZFYVE16, and TSSC1 were significant in predicting survival, and STX6 was marginally significant.

TABLE 12

Cox proportion hazards analysis result of each individual DEG in predicting the survival time

| Gene | coefficient | Log-likelihood | p-value |
|---|---|---|---|
| PPFIA1 | −0.495615 | −81.970516 | 0.006833 |
| STX6 | −0.364594 | −83.825898 | 0.057583 |
| ZFYVE16 | −0.601594 | −80.710014 | 0.001710 |
| TSSC1 | 0.560327 | −81.265099 | 0.003135 |

The p-values in this table show that PPFIA1, ZFYVE16, and TSSC1 are significant in predicting survival, and STX6 is marginally significant.

Interestingly, FLT3 Mutation is a good indicator of the differentially expressed behavior of each DEG between the Short and the Long groups, as shown in Table 10. That is, based on patients' responses to each of the four non-trivial molecular abnormalities (FLT3 Mutation, IDH1 R132, IDH R140 and NPMc), patients were assigned into two groups (positive vs. negative), and then t-tests were applied to see if any of the four DEGs (PPFIA1, STX6, ZFYVE16, and TSSC1) behaves differentially between these two groups. The p-values in this table show that the dependence between each of those four genes and FLT3 mutation is quite significant.

TABLE 13

| | AML biomarkers | | | | |
|---|---|---|---|---|---|
| Gene | FLT3 (23− vs. 10+) | IDH1 R132 (30− vs. 3+) | IDH1 R140 (28− vs. 5+) | NPMc (22− vs. 11+) | IDH1 R132 + R140 (25− vs. 8+) |
| PPFIA1 | 0.001805 | 0.546309 | 0.496346 | 0.770279 | 0.870110 |
| STX6 | 0.001067 | 0.501314 | 0.526484 | 0.097038 | 0.937205 |

TABLE 13-continued

| | AML biomarkers | | | | |
|---|---|---|---|---|---|
| Gene | FLT3 (23− vs. 10+) | IDH1 R132 (30− vs. 3+) | IDH1 R140 (28− vs. 5+) | NPMc (22− vs. 11+) | IDH1 R132 + R140 (25− vs. 8+) |
| ZFYVE16 | 0.002589 | 0.326286 | 0.212193 | 0.714207 | 0.084485 |
| TSSC1 | 0.008188 | 0.472596 | 0.207058 | 0.446264 | 0.120672 |

Figure 6:
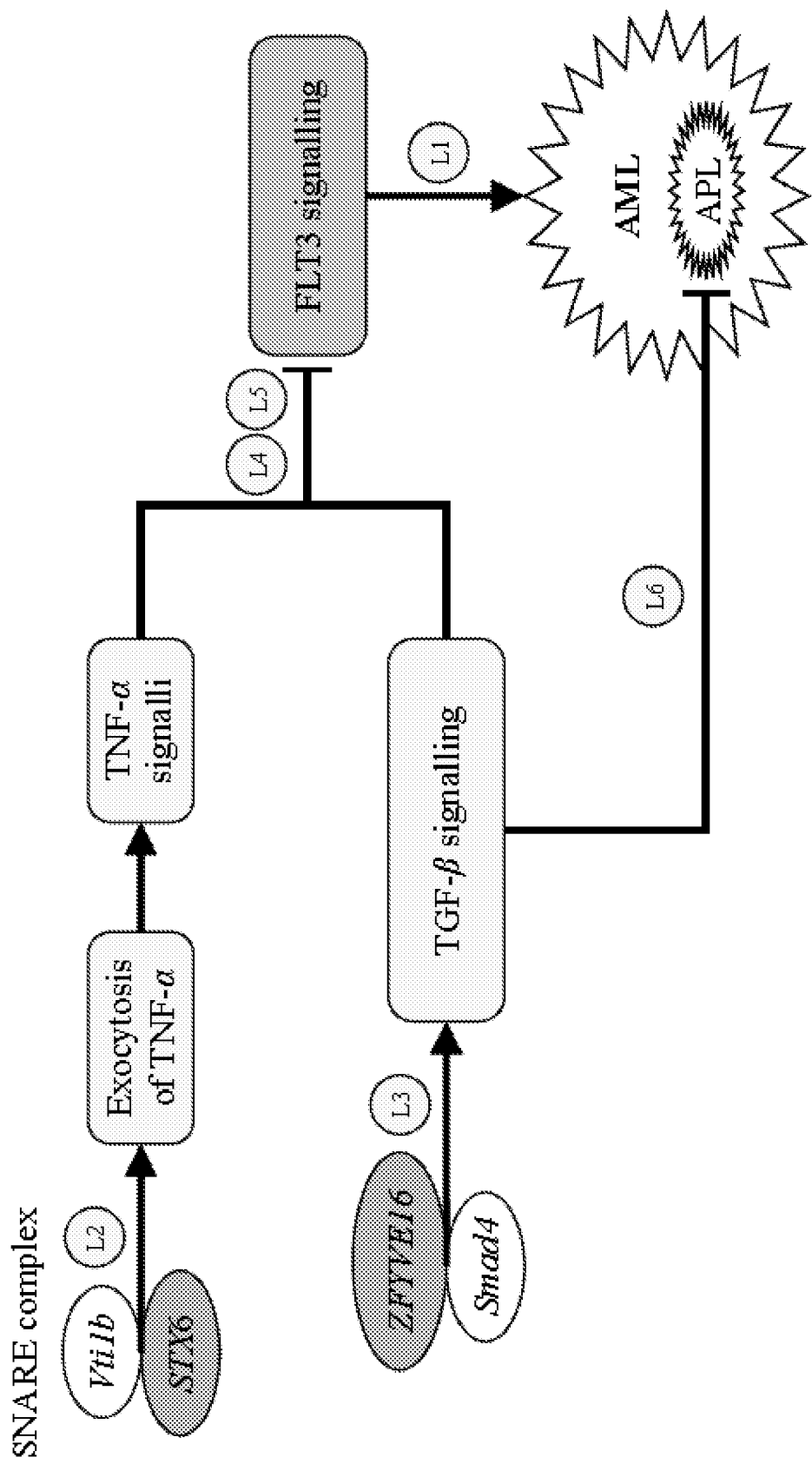
FIG. 6 is a chart illustrating that a hypothetic molecular mechanism may provide novel prognostic insights into AML.

The above quantitative analysis results along with several pieces of literature evidence allowed the generation of a hypothesis regarding the molecular mechanism underlying AML prognosis, as illustrated in FIG. 6. FLT3 is one of the most frequently mutated genes in AML. As shown in FIG. 6 at L1, the constitutive activation of FLT3 due to mutation can result in AML and Acute Lymphoblastic Leukemia (Entrez Gene Summary: www.ncbi.nlm.nih.gov/gene/2322, as of Jun. 16, 2013). STX6 and ZFYVE16 may play important roles in indirect regulations of FLT3 signaling. As shown in FIG. 6 at L2, Stx6 and Vti1b form a SNARE complex, which is up-regulated in activated murine macrophages to facilitate exocytosis of TNF-alpha. As shown in L3, ZFYVE16 encodes protein Endofin that interacts with Smad4 to facilitate TGF-beta signaling. Turning to L6, deregulated TGF-beta signaling is known to be involved in a variety of human cancers, and may also participate into leukemogenesis, especially in Acute Promyelocytic Leukemia (APL) a subtype of AML. Both TNF-alpha and TGF-beta can block FLT3-induced hematopoietic activity (L4). One study in mice suggested that the ability of FLT3 ligand to simulate the in vitro growth of primitive hematopoietic progenitors is potently and directly inhibited by TGF-beta and TNF-alpha (L5).

We applied Gene Set Enrichment Analysis (GSEA), and identified that the gene set annotated by a GO term (GO: 0017015 Regulation of TGF-beta receptor signaling pathway) was significantly up-regulated (p-value=0.048) in the Short group. Most of genes in this set are involved into negative regulation of TGF-beta receptor signaling pathway (GO:0030512) and/or negative regulation of BMP signaling pathway (GO:0030514). It should be noted that both TGF-beta and BMP belong to the TGF-beta superfamily, and there are complex cross-talks between TGF-beta receptor signaling pathway and BMP signaling pathway. GSAE analysis also showed that the subset of genes annotated by GO:0030512 or GO:0030514 was significantly up-regulated (p-value=0.048) in the Short group. This result resonates well with the identification of ZFYVE16 by Composite-Cut.

In addition, transplant may be another important factor affecting the survival time. In our chosen group, 9 out of 33 patients received transplants. To investigate (a) if there exists any relationship between transplant and those four DEGs and (b) if those four DEGs carry additional information in predicting survival time, the following dependency analysis and survival analysis was conducted:

(I) Chi-square test was applied to test if survival (Short or Long) depends on transplant status. The result showed that such a dependency is not significant (p=0.134).

(II) The dependencies between transplant and the expression levels of PPFIA1, ZFYVE16, TSSC1 and STX6 were very low according to the t-test analysis results.

(III) Transplant records combined with the continuous expression levels of PPFIA1, ZFYVE16, and TSSC1 were more significant in predicting survival than using the transplant records alone.

Therefore, it was concluded that PPFIA1, ZFYVE16, and TSSC1 can be good biomarkers in predicting survival of AML patients even when the transplant record is considered.

Analysis of RNA-Seq Data of External RNA Control Consortium (ERCC) Spike-Ins

Also, Composite-Cut was compared with other FDR control settings on another RNA-seq dataset, GSE49712. The dataset was generated by the Sequencing Quality Control Consortium from two reference RNA samples: 5 replicates of the Strategene Universal Human Reference RNA (referred as group A), and 5 replicates of the Ambion Human Brain Reference RNA (referred as group B). Ninety-two synthetic RNAs from the External RNA Control Consortium (ERCC) were added as spike-in controls to the replicates in groups A and B at known concentrations. There are four different ratios of the spike-ins between group A and group B: 1/2, 2/3, 1 and 4 (23 spike-ins at each ratio). The 23 spike-ins with ratio 1 are considered as TRUE nulls (referred as true null spike-ins), and the rest 69 spike-ins with ratios 1/2, 2/3 or 4 are considered as TRUE alternatives (referred as true alternative spike-ins). Using the ERCC spike-ins as the ground truth, we benchmarked Composite-Cut and other FDR control settings.

The gene count dataset "GSE49712_HTSeq" from GEO was used and was. pre-processed as follows. Firstly, those trivial RNAs with zero count were removed in all 10 replicates. Then LOESS normalization was applied, where the loess curves were fit to those 23 true null spike-ins. The count values were $\log^2$ transformed and the number of iterations was set to 10. A series of different FDR cutoffs was set, and Composite-Cut and other FDR control settings allowed to report the ERCC spike-ins (say, P true null spike-ins+Q true alternative spike-ins) they identified. The corresponding true positive rate (TPR) as Q/(number of true alternatives)=Q/69 and false positive rate (FPR) as P/(number of true nulls)=P/23, can be calculated as illustrated in Table 14.

TABLE 14

Comparison of Composite-Cut and other FDR control settings on the ERCC dataset. Each column lists the TPR of different settings at a false positive rate (0/23, 1/23, 2/23, or 3/23)

| | FPR | | | |
|---|---|---|---|---|
| FDR control | 0/23 | 1/23 | 2/23 | 3/23 |
| Composite-Cut | 0.739 | 0.783 | 0.812 | 0.812 |
| $SAM^T$ | 0.667 | 0.710 | 0.739 | 0.768 |
| $SAM^R$ | 0.275 | 0.638 | 0.681 | 0.783 |
| $miFDR^T$ | 0.696 | 0.725 | 0.754 | 0.768 |
| $miFDR^R$ | 0.652 | 0.783 | 0.812 | 0.812 |
| $BH^t$ | 0.710 | 0.754 | 0.754 | 0.768 |
| $BH^r$ | 0.058 | 0.783 | N/A | 0.783 |
| $Storey^t$ | 0.710 | 0.754 | 0.768 | 0.797 |
| $Storey^r$ | 0.652 | 0.783 | N/A | 0.812 |
| Best TPR | 0.739 | 0.783 | 0.812 | 0.812 |

Composite-Cut is the best at FPR=0, and tied for the best at other FPR levels. Two TPR values are marked as N/A because FPR=2/23 cannot be achieved by Storey-r and BH-r.

Therefore, a system and method is provided for utilizing an algorithmic construct referred to herein as the "Composite-Index" to integrate multiple base statistics to maximize the utilization of differential information. "Composite-Cut" was developed to detect significant features with a special case of Composite-Index. We conducted a series of comparisons on simulation datasets, DNA Microarray datasets, and RNA-seq gene expression datasets. The results were endorsed by various supplementary analyses, such as, literature search, gene ontology enrichment analysis, gene set enrichment analysis, survival analysis, dependency analysis, and classification analysis. Literary evidence suggests that the genes called significant only by Composite-Cut are indeed relevant to the underlying biology. We concluded that Composite-Cut is consistently and significantly more powerful than existing FDR control methods. In addition, Composite-Index and Composite-Cut can be widely practiced to analyze other high-dimensional datasets that require multiple comparisons correction. Although the above discussion of Composite-Cut was with respect to two base statistics, the formulation of Composite-Index is general and capable of accommodating various numbers of base statistics. However, when more than two base statistics are used, the searching method used by Composite-Cut can have a high computational complexity.

The experimental results also showed that Composite-Cut was capable of identifying relatively more subtle changes (e.g., features with small fold-changes). Such subtle changes were showed to be relevant to the underlying biology. The transcriptional changes of some genes called significant by Composite-Cut alone, can be mild (e.g. transcriptional changes within two-fold). In complex systems, detecting subtle changes can be extremely important because the systematic aggregation and propagation of subtle changes at upstream can cause dramatic downstream effects that are easier to detect. We believe that such a capability can lead to more insight, discovery, and knowledge in practice.

The present invention has been described in terms of one or more preferred embodiments, and it should be appreciated that many equivalents, alternatives, variations, and modifications, aside from those expressly stated, are possible and within the scope of the invention.

The invention claimed is:

1. A computer system for analyzing datasets comprising:
a non-transitory, computer-readable, storage medium having stored thereon a dataset having data that corresponds to a plurality of features and having stored thereon a plurality of base statistical analyses on the dataset to yield multiple, different base statistics with respect to each feature in the plurality of features;
a processor having access to the non-transitory computer-readable storage medium to access the dataset and the base statistics and having access to instructions that, when executed by the processor, cause the processor to:
use the dataset and the base statistics to find a transformation that determines significant features while controlling a false discovery rate (FDR) to be below a target FDR threshold ($\Psi$), wherein a predetermined number of the plurality of features are assumed to be independent from each other;
use the transformation, generate a composite index that represents a synthesis of the base statistics; and
generate a report indicating at least the relative presence of the significant features in the dataset using the composite index.

2. The computer system of claim 1 wherein the base statistics include K different base statistics $\vec{d}_i = [d_i^1, d_i^2, \ldots, d_i^K]$ obtained for every feature in the dataset.

3. The computer system of claim 2 wherein the processor is further caused to define the given region ($\Gamma$) as:

$$\Gamma = \Gamma^+(\tau^+) \cup \Gamma^-(\tau^-) = \{c | c \geq \tau > 0\} \cup \{c | c \leq \tau < 0\}$$

where $\tau^+$ and $\tau^-$ are cutoffs that define positive and negative bounds of the given region as $\Gamma^+ = \Gamma^+(\tau^+) = \{c | c \geq \tau < 0\}$ and $\Gamma^- = \Gamma^-(\tau^-) = \{c | c \leq \tau < 0\}$, respectively.

4. The computer system of claim 3 wherein the processor is further caused to control positive and negative FDR separately.

5. The computer system of claim 4 wherein finding the transformation includes finding a first transformation for a positive side and second transformation for negative side to compensate for the base statistics having different tail characteristics at the positive side relative to the negative side.

6. The computer system of claim 2 wherein $\mathbb{C}_{f(\cdot)} = \{c_i = f(\vec{d}_i)\}_{i=1,\ldots,M}$ denotes the composite index set for all M features in the dataset, $FDR(\Gamma, f(\cdot))$ denotes FDR over the given region ($\Gamma$), and $D(\Gamma, f(\cdot))$ denotes the number of significant features.

7. The computer system of claim 6 wherein the transformation $f(\cdot)$ gives rise to $\mathbb{C}$ so that the expected number of significant features is maximized while $FDR_{f(\cdot)}(\Gamma)$ is smaller than the FDR threshold ($\Psi$), such that the processor is caused to find at least one of:

$$\max_{\Gamma, f(\cdot)} |D(\Gamma, f(\cdot))| \text{ Satisfy } FDR(\Gamma, f(\cdot)) < \Psi; \text{ or}$$

$$\max_{\Gamma^-, f^-(\cdot)} |D(\Gamma^-, f^-(\cdot))| + \max_{\Gamma^+, f^+(\cdot)} |D(\Gamma^+, f^+(\cdot))|$$

$$\text{Satisfy } FDR(\Gamma^-, f^-(\cdot)) < \Psi \text{ \& } FDR(\Gamma^+, f^+(\cdot)) < \Psi;$$

wherein $\tau^+$ and $\tau^-$ are computationally decided cutoffs.

8. The computer system of claim 7 wherein the FDR threshold ($\Psi$) is user-defined.

9. The computer system of claim 7 wherein the feature threshold value is computed to maximize the number of significant features in the dataset.

10. The computer system of claim 1 wherein the dataset includes gene expression data.

11. The computer system of claim 1 wherein the plurality of features is all features and the significant features determined are maximized.

12. A microarray analysis system comprising:
a microarray configured to hold a biological material to assay the biological material and generate a dataset about the biological material based thereon;
a processor configured to:
perform a plurality of base statistical analyses on the dataset to yield multiple, different base statistics with respect to each of a plurality of features;
use the dataset and the base statistics to find a transformation that determines significant features while controlling a false discovery rate (FDR) to be below a target FDR threshold ($\Psi$), wherein a predetermined number of the plurality of features are assumed to be independent from each other;

using the transformation, generate a composite index that represents a synthesis of the base statistics; and generate a report indicating at least the relative presence of the significant features in the dataset using the composite index.

13. The system of claim 12 wherein the assay is performed with respect to at least one of DNA fragments, antibodies, or proteins of the biological material.

14. The system of claim 12 wherein the base statistics include K different base statistics $\vec{d}_i = [d_i^1, d_i^2, \ldots, d_i^K]$ obtained for every feature in the dataset.

15. The system of claim 14 wherein the processor is further caused to define the given region ($\Gamma$) as:

$$\Gamma = \Gamma^+(\tau^+) \cup \Gamma^-(\tau^-) = \{c | c \geq \tau > 0\} \cup \{c | c \leq \tau < 0\}$$

where $\tau^+$ and $\tau^-$ are cutoffs that define positive and negative bounds of the given region as $\Gamma^+ = \Gamma^+(\tau^+) = \{c | c \geq \tau < 0\}$ and $\Gamma^- = \Gamma^-(\tau^-) = \{c | c \leq \tau < 0\}$, respectively.

16. The system of claim 15 wherein the processor is further caused to control positive and negative FDR separately.

17. The system of claim 16 wherein finding the transformation includes finding a first transformation for a positive side and second transformation for negative side to compensate for the base statistics having different tail characteristics at the positive side relative to the negative side.

18. The system of claim 13 wherein the transformation $f(\bullet)$ gives rise to $\mathbb{C}$ and cutoffs ($\tau^+, \tau^-$) so that the expected number of significant features is maximized while $FDR_{f(\bullet)}(\Gamma)$ is smaller than the FDR threshold ($\Psi$), such that the processor is caused to find at least one of:

$$\max_{\Gamma, f(\cdot)} |D(\Gamma, f(\cdot))| \text{ Satisfy } FDR(\Gamma, f(\cdot)) < \Psi; \text{ or}$$

$$\max_{\Gamma^-, f^-(\cdot)} |D(\Gamma^-, f^-(\cdot))| + \max_{\Gamma^+, f^+(\cdot)} |D(\Gamma^+, f^+(\cdot))|$$

Satisfy $FDR(\Gamma^-, f^-(\cdot)) < \Psi$ & $FDR(\Gamma^+, f^+(\cdot)) < \Psi$.

19. The system of claim 13 wherein the multiple, different base statistics include a t-statistic, a ranksum statistic, a corrected t-statistic and a corrected ranksum-test statistic.

20. The system of claim 13 wherein the composite index represents a combination of the multiple, different base statistics.

21. The system of claim 13 wherein the transformation ($f(\bullet)$) can be represented as $w_1 d_i^T + w_2 d_i^R$, where $w_1 \geq 0$ and $w_2 \geq 0$ satisfying $w_1 + w_2 = 1$ and, wherein the processor is caused to examine all possible combinations of $\langle \alpha, \beta \rangle$ and cutoff $\tau$ at a predetermined degree of granularity to find one combination that identifies a maximal number of significant features and satisfies the FDR threshold ($\Psi$).

22. The system of claim 21 wherein the transformation ($f(\bullet)$) includes a positive transform ($f^+(\bullet)$) and a negative transform ($f^-(\bullet)$) and the processor is caused to examine a set of $\langle w_1, w_2 \rangle$, such that, for each $\langle w_1, w_2 \rangle$ pair, the processor identifies a positive threshold $\tau^+$ that yields a largest number of positive significant features $$\left( \max_{\Gamma^+, f^+(\cdot)} D(\Gamma^+, f^+(\cdot)) \right)$$

satisfying $FDR(\Gamma^+, f^+(\bullet)) < \Psi$ and a negative threshold $\tau^-$ that yields a largest number of negative significant features $$\left( \max_{\Gamma^-, f^-(\cdot)} D(\Gamma^-, f^-(\cdot)) \right)$$

satisfying $FDR(\Gamma^-, f^-(\bullet)) < \Psi$.

23. The system of claim 22, wherein the processor is caused to identify a $\langle \alpha, \beta \rangle$ pair as optimal if a number of significant features identified under this condition is the largest among all examined pairs.

24. The system of claim 12 wherein the predetermined number of features is all features.

* * * * *

UNITED STATES PATENT AND TRADEMARK OFFICE
CERTIFICATE OF CORRECTION

| | | |
|---|---|---|
| PATENT NO. | : 11,055,304 B2 | Page 1 of 1 |
| APPLICATION NO. | : 15/518403 | |
| DATED | : July 6, 2021 | |
| INVENTOR(S) | : Pengyu Hong et al. | |

It is certified that error appears in the above-identified patent and that said Letters Patent is hereby corrected as shown below:

In the Specification

Column 8, Line 54, "$\widehat{FDR}_{\lambda, \mathbb{C}_\lambda, \mathbb{C}}(\Gamma) = 0$" should be --$\widehat{FDR}_{\lambda, \mathbb{C}}(\Gamma) = 0$--.

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*